United States Patent
Ainger et al.

(10) Patent No.: US 11,415,541 B2
(45) Date of Patent: Aug. 16, 2022

(54) ELECTRICAL IMPEDANCE HEMATOCRIT AND HBA1C BIOSENSOR COMPRISING SAMPLE PLATE AND SAMPLE APPARATUS

(71) Applicant: Smartcare Technologies Ltd, Crowborough (GB)

(72) Inventors: Phillip J. Ainger, Dyfed (GB); Matthew Robert Bryan, Shipley (GB)

(73) Assignee: SMARTCARE TECHNOLOGIES LTD, East Sussex (GB)

( * ) Notice: Subject to any disclaimer, the term of this patent is extended or adjusted under 35 U.S.C. 154(b) by 164 days.

(21) Appl. No.: 16/827,822

(22) Filed: Mar. 24, 2020

(65) Prior Publication Data
US 2020/0240945 A1   Jul. 30, 2020

Related U.S. Application Data

(62) Division of application No. 14/394,176, filed as application No. PCT/GB2013/050957 on Apr. 12, 2013, now Pat. No. 10,641,724.

(30) Foreign Application Priority Data

Apr. 13, 2012  (GB) ..................... 1206588

(51) Int. Cl.
*G01N 27/327* (2006.01)
*G01N 33/487* (2006.01)
(Continued)

(52) U.S. Cl.
CPC ....... *G01N 27/3271* (2013.01); *G01N 27/416* (2013.01); *G01N 33/48707* (2013.01); *G01N 33/492* (2013.01)

(58) Field of Classification Search
CPC ............. G01N 27/3271; G01N 27/416; G01N 33/48707; G01N 33/492; G01N 27/07;
(Continued)

(56) References Cited

U.S. PATENT DOCUMENTS 5,526,808 A   6/1996   Kaminsky
5,801,307 A   9/1998   Netzer
(Continued)

FOREIGN PATENT DOCUMENTS

DE   102007022323 A1   11/2008
EP       0417796         3/1991
(Continued)

OTHER PUBLICATIONS

Son, et al., Fabrication of a Disposdable Biochip for for Measuring Percent Hemoglobin A 1 c (%Hb A 1 c), Science Direct, Mar. 29, 2006.
(Continued)

*Primary Examiner* — Xiuyu Tai
(74) *Attorney, Agent, or Firm* — Niels Haun; Dann, Dorfman, Herrell & Skillman, P.C.

(57) ABSTRACT

A sampling plate (1) is provided comprising a sample zone (2) for receiving a liquid sample, and two drive electrodes (3, 4) with separate respective electrode terminals spaced by a spacing for receiving a the liquid sample within the sample zone for use in driving an electrical signal through the sample. Two sensing electrodes (5, 6) are provided with separate respective electrode terminals spaced between the electrode terminals of the two drive electrodes for use in sensing an electrical signal generated by the drive electrodes within a the sample. A sampling apparatus (15) is provided for use with the plate.

17 Claims, 6 Drawing Sheets

(51) Int. Cl.
*G01N 33/49* (2006.01)
*G01N 27/416* (2006.01)

(58) Field of Classification Search
CPC .. G01N 33/49; G01N 33/723; G01N 27/3273; G01N 27/3272; G01N 27/3274; G01N 33/48757; G01N 27/06; G01N 33/86; G01N 33/48785; G01N 2333/755; G01N 15/0656; G01N 33/5438; C12Q 1/001; C10Q 1/006; B01L 3/502715; B01L 2200/04; B01L 2300/0864; B01L 2300/0887; B01L 2400/0406; B01L 2300/0645; B01L 2300/0825; H05K 3/027; H05K 1/0393; Y10T 29/49156; Y10T 29/49155; Y10T 29/49117
See application file for complete search history.

(56) References Cited

U.S. PATENT DOCUMENTS

| | | |
|---|---|---|
| 6,058,934 A | 5/2000 | Sullivan |
| 8,128,801 B2 | 3/2012 | Mansouri |
| 2004/0079652 A1 | 4/2004 | Vreeke |
| 2004/0256248 A1 | 12/2004 | Burke |
| 2005/0103624 A1 | 5/2005 | Bhullar |
| 2007/0227911 A1 | 10/2007 | Wang |
| 2008/0297169 A1 | 12/2008 | Greenquist |
| 2010/0089774 A1 | 4/2010 | Manohar |
| 2010/0089775 A1 | 4/2010 | Chen |
| 2011/0048972 A1 | 3/2011 | Moffat |
| 2011/0139634 A1 | 6/2011 | Chou |
| 2011/0168575 A1 | 7/2011 | Lica |
| 2011/0241694 A1 | 10/2011 | Burke |
| 2012/0111739 A1 | 5/2012 | Pasqua |

FOREIGN PATENT DOCUMENTS

| | | |
|---|---|---|
| EP | 1111378 | 6/2001 |
| EP | 2211170 | 7/2010 |
| JP | 03020657 A | 1/1991 |
| JP | 2008076143 | 4/2008 |
| WO | 03017834 | 3/2003 |
| WO | 2006017446 | 2/2006 |
| WO | 2009003691 | 1/2009 |
| WO | 2011124906 A1 | 10/2011 |
| WO | 2012006778 | 1/2012 |

OTHER PUBLICATIONS

Pop Gheorghe A. et al.; Catheter-based impedance measurements in the right atrium for continuously monitoring hematocrit and estimating blood viscosity changes; an in vivo feasibility study in swine; Biosensors and Bioelectronics 19 (2004) 1685-1693.

Cha et al.; An electronic method for rapid measurement of haematocrit. in blood samples Physiol. Meas. 15 (1994)12g, . . . 137, Printed in the UK.

Australian Examination Report from corresponding Australian Application No. 2016216538 dated Feb. 19, 2018.

United Kingdom Search and Examination report dated Nov. 29, 2017.

European Examination Report for corresponding Application No. GB1206588.4, dated May 10, 2017.

European Search report from EP application No. 15 188 852.6 dated Feb. 29, 2016.

GB Search Report dated Sep. 5, 2013 corresponding to GB 1206588.4.

The International Search Report and Written Opinion dated Aug. 27, 2013 corresponding to PCT/GB2013/050957.

Output (HCT or HbA1c)

ELECTRICAL IMPEDANCE HEMATOCRIT AND HBA1C BIOSENSOR COMPRISING SAMPLE PLATE AND SAMPLE APPARATUS

RELATED APPLICATIONS

This application is divisional of U.S. application Ser. No. 14/394,176, filed Oct. 13, 2014, which in turn is a 371 application of International Application No. PCT/GB2013/050957 filed Apr. 12, 2013, which claims the benefit of priority of United Kingdom Patent Application No. 1206588.4 filed Apr. 13, 2012. Each of the foregoing applications is hereby incorporated herein by reference.

FIELD OF THE INVENTION

The present invention relates to a sample measurement system. In particular, the present invention relates to the measurement of properties of liquid samples of (or containing) blood. In particular the invention relates to a sample measurement system for measuring certain selected properties of a liquid substrate, such as the glucose levels in a blood sample. The invention also relates to a sampling plate, a measurement device, a data carrier containing software to operate the measurement device.

BACKGROUND OF THE INVENTION

There is a widespread need for improving the accuracy of sample measurement systems such as those enabling e.g. a diabetes sufferer to know their blood sugar levels—i.e. the concentration of glucose in their blood.

Existing sample measurement systems use a measurement device which receives and takes measurement readings from a sampling plate spotted with a blood sample from a user. The sampling plate is often rectangular and is end-loaded with the blood sample. The blood sample, once loaded, is usually drawn into a sample zone having a number of sampling zones from which measurements are taken by the system.

Each sampling zone typically has its own particular contents. For example, the first sampling zone may have a glucose oxidase deposit within it, a second deposit comprising a mixture of glucose oxidase and a predetermined amount of glucose, while a third sampling zone may contain no deposit. As the blood sample is drawn over all three sampling zones, chemical reactions occur with the deposits in each sampling zone, resulting in discrete electrolytes. Each sampling zone bridges a corresponding pair of electrodes. A potential difference is established across each sampling zone, via the electrodes, when the sampling plate is inserted into an operating measurement device. Electric current readings for each sampling zone then provide measurements necessary to assess the blood sugar (glucose) levels. For instance, the first sampling zone may give the primary measurement, whereas the second sampling zone may provide a degree of calibration since a known quantity of glucose was already present there. The third zone may give a final check by accounting for the non-glucose contribution to the measurements in the first and second sampling zones.

However, in spite of these calibrations and final checks, error margins in such blood glucose readings are still high. Indeed, blood glucose levels are strongly influenced by the fluctuating and transient glucose levels in the plasma of the blood sample, which may not be representative of the long-term blood glucose levels of the patient and may, rather, simply indicate a recent transient rise or drop in blood glucose levels within the blood plasma of the patient e.g. due to recent food consumption of other short-term environmental factors.

The present invention aims to address this.

Blood plasma is the liquid component of blood in which the blood cells in whole blood are normally suspended. Blood plasma typically constitutes about 55% of the total volume of the blood. It is the extracellular fluid part of blood and is mostly water but contains dissolved glucose and other contents.

The volume percentage of red blood cells in blood is known as the haematocrit (HCT). Other terms for this are the packed cell volume (PCV) or erythrocyte volume fraction (EVF). Haematocrit is normally about 45% for men and 40% for women. The haematocrit is typically calculated by multiplying the red blood cell count in a blood sample by the average cell volume, then dividing the result by the whole blood sample volume.

Glycated haemoglobin (a.k.a. haemoglobin A1c, HbA1c, or just A1c) is a form of haemoglobin measured primarily to identify the average plasma glucose concentration over prolonged periods of time. It is formed in a non-enzymatic glycation pathway by hemoglobin's exposure to plasma glucose. Normal levels of glucose produce a normal amount of glycated hemoglobin. As the average amount of plasma glucose increases, the fraction of glycated hemoglobin increases. This serves as a marker for average blood glucose levels over the previous months prior to the measurement. Liquid chromatography and capillary electrophoresis are two ways of measuring glycated haemoglobin (HbA1c). Both methods are complex, expensive and wholly unsuited for easy and simple implementation by a patient.

BRIEF SUMMARY OF THE INVENTION

At its most general, the invention in one aspect is a system (method and/or apparatus) to measure haematocrit of a liquid sample containing blood according to the electrical impedance (e.g., resistance and reactance) it has in response to an alternating electrical potential difference applied across the sample. The measured haematocrit may be used to improve the accuracy of blood glucose measurements of the blood in another aspect of the invention. It has been found that applying an alternating potential difference (voltage) across such a sample results in a resistance and/or a reactance which is surprisingly responsive to haematocrit. The invention exploits this finding. The presence of red blood cells within a blood sample complicates the interpretation of blood glucose measurements using existing methods. The invention may remove or reduce that complication to enable more accurate blood glucose measurements to be made. At its most general, the invention in another aspect is a system (method and/or apparatus) to measure a level of glycated haemoglobin (HbA1c) in a liquid sample containing blood according to the electrical impedance (e.g., resistance and reactance) it has in response to an alternating electrical potential difference applied across the sample. It has been found that applying an alternating potential difference (voltage) across such a sample results in a resistance and/or a reactance which is surprisingly responsive to HbA1c of the sample. The invention exploits this finding.

In a first of its aspects, the invention may provide a sampling plate comprising a sample zone for receiving a liquid sample. The sampling plate may have two drive electrodes with separate respective electrode terminals spaced by a spacing for receiving the liquid sample within the sample zone for use in driving an electrical signal through the sample. Two sensing electrodes may be provided with separate respective electrode terminals spaced between the electrode terminals of the two drive electrodes for use in sensing an electrical signal generated by the drive electrodes within a the sample.

Herein, a "sampling plate" may mean any surface capable of receiving a liquid sample in a sample zone. Preferably, however, the sampling plate is portable. Suitably the sampling plate may cover an area less than 1 $m^2$, preferably less than 50 $cm^2$, more preferably less than 10 $cm^2$ and most preferably less than 5 $cm^2$. The sampling plate may cover an area less than 500 $mm^2$—for instance 350 $mm^2$ where the sampling plate is 10 mm wide by 35 mm long. Suitably the sampling plate may be rectangular. The sampling plate may be a strip, and may be a flexible strip. Preferably, however, the sampling plate is an individual plate, preferably a rigid sampling plate. The thickness of the sampling plate is preferably less than 1 cm, preferably less than 1 mm, more preferably less than 0.5 mm, most preferably less than 0.25 mm.

The sampling plate is preferably compatible with a measurement device. For example, the measurement device is preferably operable to communicate with the sampling plate to measure one or more selected properties of the sample. Preferably the sampling plate may be inserted into the measurement device to allow measurements to be taken.

The two sensing electrode terminals may present to each other opposing sides which define between them an elongate sensing gap extending along the sample zone for receiving at least parts of the sample therein. The sensing electrode terminals may be substantially flat and side-by-side to define a substantially flat sensing gap. The width of the two sensing electrode terminals is preferably the same. That width is preferably about double the size of the sensing gap between them.

The two drive electrode terminals may present to each other opposing sides which define between them an elongate drive gap extending along the sample zone for receiving at least parts of the sample therein whereby the drive electrodes are adapted to drive electrical signal transversely across the drive gap. The drive electrode terminals may be substantially flat and side-by-side to define a substantially flat drive gap.

The sensing gap may extend along the drive gap. The sensing gap and/or the drive gap may preferably have a substantially uniform width along at least a part of its length.

A drive electrode terminal and an adjacent sensing electrode terminal may be arranged in/on the sampling plate so that they present to each other opposing sides which define between them an elongate partitioning gap. Preferably, this partitioning gap extends along the sample zone to define a partition between those adjacent terminals within the sample zone. This may apply to each of the drive electrode terminals and their respective adjacent/neighbouring sensing electrode terminal.

The partitioning gap preferably has a substantially uniform width along at least a part of its length, preferably substantially all of its length. Each partitioning gap width is preferably the same size. Preferably the partitioning gap width is about 1% times the width of the sensing gap.

The sensing electrode terminals may be formed on a surface of the sensing plate within the sample zone. Preferably, the drive electrode terminals are formed on a surface of the sensing plate in common with the sensing electrode terminals within the sensing zone. The electrodes may be formed upon the sampling plate by a known printing process. However, for a better degree of accuracy or consistency a technique known as laser ablating is preferably used to remove electrode material (e.g. Gold) formed as a sheet/coating onto a surface of the sampling plate, where the electrode gaps are required. Preferably, in production, conductive electrode material may be laid down on a surface area on one side of the sampling plate with no gap features, and the gaps may then be laser ablated to define the electrodes.

The sampling plate is preferably arranged to be detachably attachable electrically to electrical apparatus adapted for supplying the drive current to the drive electrodes and for taking measurements via the sensing electrodes. In this regard, preferably each of the drive electrodes and each of the sensing electrodes is in electrical communication with respective electrical contacts provided on the sampling plate which are exposed for electrical connection simultaneously with an external drive current source and external sensing circuitry, respectively, of such an apparatus.

Preferably, the width of the sensing gap is greater than about 90 microns and less than about 160 microns. Preferably the width of the partitioning gap is about 1.5 times the width of the sensing gap. An alternating potential difference is preferably applied across a gap between two electrodes designed to be bridged by a sample being measured. It has been found that a careful dimensioning of the sensing gap and the drive gap enhances the accuracy of haematocrit measurement greatly, and also permits HbA1c to be measured. The gap size is preferably substantially smaller than a gap size between electrodes typically employed in existing systems designed to measure blood glucose. Preferably, the sensing gap is wider than the average width of a human red blood cell, but less than the average width of two such cells.

It is postulated, but not asserted, that the sensing gap serves to form a generally linear array of red blood cells along it in which the array is generally one cell in width—this being constrained by the width of the sensing gap—and that the parts of the sensing gap not occupied by red blood cells are occupied by blood plasma. Blood plasma is typically more electrically conductive than are red blood cells at certain electrical signal frequencies. By applying an oscillating voltage, red blood cells remain mobile (e.g. oscillate) within the gap and may not coat one or other of the electrodes. The result may be that there is maintained within the sensing gap a defined linear array of red blood cells mobile within conductive blood plasma. The proportion of red blood cells within the gap, relative to the quantity of blood plasma there, influences the quantity of electrically conductive pathways (through plasma, around blood cells) available to currents applied. This may manifest itself as an electrical impedance value (e.g. resistance, reactance) determined by a haematocrit value and/or an HbA1c value, as has been observed.

The sample zone may comprise a reagent to react with free glucose in the liquid sample. This may be so when the sampling plate is intended for use in measuring a value representing the concentration of glycated haemoglobin (HbA1c) in the liquid sample as described below. The reagent may be a deposit formed on one (e.g. exclusively) of the drive electrodes in the sample zone (e.g. the one for use as an anode) to be directly accessible to a sample therein. The deposit may be in the form of an ink or paste. Preferred reagents are oxidising agents. Most preferred are enzymes and especially preferred are glucose oxidase (GOx) and glucose dehydrogenase (GDH). Where no such reagent is present, the sampling plate may be used for measuring haematocrit as described below.

The sampling plate may comprise a further sample zone containing a pair of drive electrodes as described above, and a pair of sensing electrodes as described above. The further sample zone may be free of any reagent and be intended for use in measuring HCT of a blood sample, while the other sample zone may contain the reagent and be intended for concurrent or sequential measurement of HbA1c of the same sample.

Alternatively, the drive electrode terminals of the further sample zone may comprise only one pair of drive electrodes which may present to each other, across a respective spacing, opposing electrode sides extending along the sample zone. The further sample zone may contain the reagent and be intended for use in measuring blood glucose levels within the plasma of a blood sample. These opposing sides may define between them a drive gap for receiving a sample therein. This spacing may define a gap which is preferably greater than about 200 microns in width, and may be between 200 microns and 400 microns in width. This dimensioning has been found to be preferable for the electrodes in sampling zones containing the reagent to react with free glucose in the liquid sample, and for measuring a current generated in response to a direct (DC) drive voltage applied across the drive gap. The measured current may be used to determine a measure of the glucose in the blood plasma of the sample.

The opposing sides in the pair of drive electrodes of the further sample zone may be of unequal length. They may be curved. One side may be convex and the opposing side reciprocally concave and of greater length than the convex side. Preferably the electrode with the longer side is used as the cathode of the pair. This is preferable in view of the greater gap size in each further pair of electrodes. It has been found that electrical currents driven across those wider gaps through a blood sample are more prone to diffuse in a direction along the gap rather than flowing directly across the gap un-deviated. In order to better capture diffused charges (current) in the blood sample the electrode to which the charges flow when a direct (DC) voltage is applied between the electrodes, has the longer edge. The spacing of the drive gap may be substantially uniform along at least a part of its length.

In a second of its aspects, the invention may provide a sampling apparatus for use in performing electrical measurements on a liquid sample containing blood, including two current output terminals for outputting an alternating current signal applied therebetween, and an alternating electrical current unit in electrical communication with the two current output terminals for applying thereto an alternating electrical current of a given amplitude and frequency when a liquid sample is in electrical connection between the two current output terminals.

The sampling apparatus may include a voltage unit in electrical communication with the two current output terminals for applying therebetween a direct (DC), being most preferably a substantially constant (DC), electrical potential difference of a given magnitude. A first voltage input terminal may be provided for receiving a first electrical signal externally input thereto and a separate second voltage input terminal for receiving a second electrical signal externally input thereto when the liquid sample is in electrical connection between the first and second voltage input terminals. The apparatus may include voltage detector(s) for measuring a first voltage and a second voltage using said first and second electrical signals, respectively.

A control unit may be arranged in the sampling apparatus to control the electrical current unit to apply the alternating electrical current of given frequency and concurrently to control the voltage unit and the voltage detector(s) to measure the first and second voltages both when the direct (e.g. substantially constant) DC electrical potential difference is applied and when the direct DC electrical potential difference is not applied.

A calculating unit may be arranged in the sampling apparatus to calculate a first electrical impedance (e.g. reactance) value using the first and second voltages measured when the direct (e.g. substantially constant) DC electrical potential difference is applied, and to calculate a second electrical impedance (e.g. reactance) value measured when the direct DC electrical potential difference is not applied.

The calculating unit may be arranged in the sampling apparatus to generate a value representing the concentration of glycated haemoglobin (HbA1c) in the liquid sample according to the first electrical reactance value, the second electrical reactance value and a value representing the relative volume of red blood cells in the liquid sample (haematocrit, HCT).

The calculating unit may be arranged to generate a value representing the concentration of glycated haemoglobin (HbA1c) in the blood within the sample according to the first electrical reactance value, the second electrical reactance value and a value of the relative volume of red blood cells in the liquid sample (haematocrit, HCT) according to the following formula, and store the result and/or to output the result to the user:

$$HbA1c = 100 \times \left(1 - \frac{X_1}{HCT \times X_2}\right).$$

The haematocrit value HCT may be a contemporaneously measured value, such as measured using a sample of the blood on the sampling plate, or may be a predetermined value which is generated independently of the sampling unit.

The quantity $X_1$ is considered to represent the reactance of a blood sample due to glycated red blood cells in the blood within the first sampling zone from which free glucose has been substantially oxidized by the reagent, whereas $X_2$ is considered to represent the reactance of the whole blood sample in which both plasma and red blood cells contain glucose. The proportion of that reactance due to red blood cells is considered to be represented by the term $(HCT) \times (X_2)$ according to the haematocrit of the sample.

The given frequency preferably has a value in the range 500 KHz to 1.5 MHz, e.g. about 1 MHz. More preferably, the given frequency has a value in the range 750 KHz to 1.25 MHz, yet more preferably the given frequency has a value in the range 850 KHz to 1.15 MHz, even more preferably the given frequency has a value in the range 900 KHz to 1.1 MHz, yet even more the given frequency has a value in the range 970 KHz to 1.03 MHz. It has been found that a frequency of about 1 MHz works especially well, and frequencies reasonably close to this value are desirable, though the ranges given above have been found to be acceptable in terms of accuracy of measurement in implementing the invention. The value of the direct (DC) voltage may be a value in the range from about 0.01 volts to about 1.0 volts, or preferably from about 0.1 volts to about 0.5 volts, or more preferably from about 0.2 volts to about 0.3 volts—e.g. about 0.25 volts.

It is postulated, but not asserted, that the presence of a direct (DC) voltage across the drive gap, and therefore across the sensing gap, has the effect of polarizing or physically aligning in a common direction those red blood cells that are not glycated, while the glycated red blood cells are not forced into this alignment and remain largely unaffected by the direct voltage applied across the sample. The consequence is felt most keenly when an alternating (AC) current is applied to the blood sample while the is concurrently subjected to this DC voltage. The result is believed to be that the un-glycated red blood cells aligned by the applied DC voltage are far less responsive to the AC current concurrently applied (i.e. less able to dynamically interact/oscillate in response to it) than are the glycated red blood cells. The result is that the portion of the impedance (e.g. reactance) of the blood sample arising from the un-glycated red blood cells falls dramatically, leaving the glycated red blood cells to dominate the impedance of the sample. By comparing this impedance value to the impedance value of the same sample measured when no direct (DC) voltage is applied (and thus, no un-glycated cell alignment occurs) provides a route to determining the proportion of glycated red blood cells in the sample and, from that, a measurement of HbA1c.

Alternatively, or additionally, the calculating unit may be arranged to generate a value representing the relative volume of red blood cells in the liquid sample (haematocrit) according to electrical impedance (e.g. resistance and reactance) values measured thereby from the sample. The calculating unit may be arranged to generate a value representing the concentration of glycated haemoglobin in the liquid sample according thereto.

In a third aspect, the invention may provide a sampling apparatus for use in performing electrical measurements on a liquid sample containing blood, the apparatus comprising two current output terminals for outputting an alternating current signal applied therebetween, and an alternating electrical current unit in electrical communication with the two current output terminals for applying therebetween an alternating electrical current of a given amplitude and frequency, when a liquid sample is in electrical connection between the two current output terminals.

This sampling apparatus may include a first voltage input terminal for receiving a first electrical signal externally input thereto and a separate second voltage input terminal for receiving a second electrical signal externally input thereto, when said liquid sample is in electrical connection between the first and second voltage input terminals, and a voltage detector(s) for measuring a first voltage and a second voltage using said first and second electrical signals, respectively.

A control unit may be arranged in this sampling apparatus to control the electrical current unit to apply the alternating electrical current at a first frequency and concurrently to control the voltage detector(s) to measure the first and second voltages, and to further control the electrical current unit to apply the alternating electrical current at a second frequency exceeding the first frequency and concurrently to control the voltage detector(s) to measure the first and second voltages. The first frequency may be a value (e.g. 50 KHz) within a first continuous range of values from about 1 KHz to about 150 KHz. More preferably, the first frequency has a value in the range 25 KHz to 125 KHz, yet more preferably the first frequency has a value in the range 35 KHz to 100 KHz, even more preferably the first frequency has a value in the range 45 KHz to 75 KHz, yet even more the first frequency has a value in the range 47 KHz to 53 KHz. It has been found that a frequency of about 50 KHz works especially well, and frequencies reasonably close to this value are desirable, though the ranges given above have been found to be acceptable in terms of accuracy of measurement in implementing the invention.

The second frequency may be a value (e.g. 1 MHz) within a second continuous range of values from about 500 KHz to about 1.5 MHz. More preferably, the second frequency has a value in the range 750 KHz to 1.25 MHz, yet more preferably the second frequency has a value in the range 850 KHz to 1.15 MHz, even more preferably the second frequency has a value in the range 900 KHz to 1.1 MHz, yet even more the second frequency has a value in the range 970 KHz to 1.03 MHz. It has been found that a second frequency of about 1 MHz works especially well, and frequencies reasonably close to this value are desirable, though the ranges given above have been found to be acceptable in terms of accuracy of measurement in implementing the invention.

In general, the preferred range of frequencies, and the preferential frequency within such a range, is influenced to some extent by geometrical considerations of the sampling process. Factors such as the size of surface area of conductive elements/electrodes within a test area of a sampling plate, in relation to the size of surface area of non-conductive/non-electrode parts between electrodes, can influence the position and extent of the suitable AC signal frequency ranges. These surface areas may typically be located within a sampling area, well or zone within a sampling plate which is between about 0.5 mm and 5 mm in diameter or width, or more preferably between about 1 mm and 3 mm, such as about 1.6 mm in diameter or width. These dimensions enable a sample size which is large enough to do reliable measurement upon, but does not result in a sampling size (or sampling plate size) which is too large for these purposes, or for practical use generally.

This sampling apparatus may include a calculating unit arranged to calculate a first electrical impedance (e.g. resistance and/or reactance) value using the first and second voltages measured at the first frequency, and a second electrical impedance (e.g. resistance and/or reactance) value and a reactance value using the first and second voltages measured at the second frequency. The first electrical impedance may be a resistance value ($R_1$, ohms). The second impedance may be comprise both a resistive part ($R_2$, ohms) and a reactive part ($X_3$, ohms). The calculating unit may be arranged to generate a value representing the relative volume of red blood cells in the liquid sample (haematocrit, HCT) according to the first and second electrical resistance values ($R_1$, $R_2$) and the electrical reactance value ($X_3$).

The sampling apparatus may be arranged to calculate HCT according to the following equation:

$$HCT = \left[ A\ln\left(\frac{R_1}{R_2}\right) + B\ln(X_3 + X_0) - C \right].$$

The quantities A, B and C are preferably constants associated with a sampling plate design in use. For example, the values of A, B and C may each typically be within the range from about 0.05 to about 0.5, or preferably between about 0.1 and 0.25, or more preferably between about 0.1 and about 0.2. For example, the electrodes of the sampling sheet may be formed from a conductive material (e.g. a metal such as Gold) having a sheet resistance of 5 ohms per square, the values in question may be: A=0.142; B=0.155; C=0.157. The value of the term A has been found to be affected by the electrical properties of the electrodes of the sampling plate (e.g. drive electrode terminals and/or sensing electrode terminals) within the sampling zone(s). Different properties such as conductivity (e.g. sheet resistance), the electrical voltages and currents applied to the electrodes in the sampling zone(s), and the geometry (e.g. widths) of the drive electrode terminals and sensing electrode terminals. The value of the term B has been found to be affected by the nature of the interaction and interface between the blood sample and the sampling strip surface in the sampling zone. For example, the microscopic surface roughness and the "wetting ability" of the surface affect the value of this term. Also, the aspect ratio of the electrodes within the sampling zones (e.g. the blood sample "height" as compared to the area of the electrode surfaces in the sampling zone over which it is arranged) can affect the value of B—thus, the three-dimensional geometry (e.g. depth) of the sampling zone plays a role. The term C has been found to be affected by the geometry of the shape of the sample shape determined by the shape of the sampling zone, in a way similar to its influence on the term B. The electrodes may have a sheet resistance in the range from about 2 ohms per square to about 15 ohms per square.

Actual values, suited to a given sampling zone geometry and electrode structure and material, may be determined by routine calibration employing commercially available blood samples of known HCT, as will be apparent to the skilled person. The value of $X_0$ may simply be zero, or may be adjusted if necessary to improve the predictive accuracy of the equation.

The sampling apparatus may be arranged to generate both the value representing the relative volume of red blood cells in the liquid sample (haematocrit) as described above, and to generate the value representing the concentration of glycated haemoglobin (HbA1c) in a liquid sample as described above, using that haematocrit.

The sampling apparatus may include the sampling plate described above. For example, each one of the two drive electrodes of the sampling plate may be adapted to electrically connect to a respective one of the two current output terminals concurrently. Furthermore, each one of the two sensing electrodes of the plate may be adapted to electrically connect to a respective one of the first voltage input terminal and the second voltage input terminal concurrently, thereby to connect the two drive electrodes and the two sensing electrodes to the sampling apparatus simultaneously for electrical communication therewith.

In another of its aspects, the invention may provide sampling apparatus (e.g. measurement device) for use in performing electrical measurements on a liquid sample containing blood, the apparatus comprising: a first output terminal arranged for outputting an alternating (AC) electrical current; and a second output terminal arranged outputting a direct electrical voltage applied thereto (most preferably a substantially constant (DC) voltage); and voltage input terminals (e.g. two) each for receiving an input electrical voltage signal externally input thereto; and current input terminals (e.g. two) each for receiving an input electrical current signal externally input thereto. The apparatus may include a control unit arranged to apply an alternating electrical current to the first output terminal and concurrently to measure a first electrical voltage at the voltage input terminals resulting therefrom when a the liquid sample is in electrical series connection between the first output terminal and a current input terminal, and arranged to apply a direct voltage (most preferably a substantially constant electrical (DC) voltage) to the second output terminal and concurrently to measure a second electrical current at a current input terminal resulting therefrom when a liquid sample is in electrical series connection between the second output terminal and a current input terminal. A calculating unit of the apparatus may be arranged to calculate electrical resistance and/or reactance values for the sample using a value of the first electrical current and a value of the concurrently measured first voltage, and arranged to calculate a first calculated value representing the relative volume of red blood cells in the liquid sample (haematocrit) according to the calculated electrical resistance and/or reactance values; and to calculate a second calculated value representing an amount of glucose in the liquid sample according to both the first calculated value and the measured second electrical current, and to output the result. The measured second electrical current may be measured while the direct (DC) voltage is applied to a sample zone of a sampling plate that contains a deposit of reagent to react with free glucose in a blood sample when applied there for use in measuring a first value for blood glucose levels within a blood sample when there. The alternating current may be applied to a sample zone free of such reagent and for use in measuring haematocrit within a blood sample when there. The haematocrit value may be used to improve the first value for blood glucose levels within a blood sample.

In a fourth of its aspects, the invention may provide sample measurement method for performing electrical measurements on a liquid sample containing blood, the method comprising receiving the liquid sample on a sample plate comprising electrode terminals which are separated by a spacing adapted to be bridged by blood from the liquid sample and which comprise a reagent to react with free glucose in the liquid sample, and applying to the electrodes an alternating electrical current having a given frequency to generate a first alternating potential difference across the spacing between the electrode terminals. The method may include also applying between the electrode terminals a substantially constant (DC) electrical potential difference of a given magnitude, and determining a value of a first electrical reactance of the liquid sample bridging said spacing for said given frequency, then removing the substantially constant (DC) electrical potential difference from between the two electrode terminals. The method may include applying to the electrodes the alternating electrical current having the given frequency, without the DC potential applied, to generate a second alternating potential difference across the spacing between the electrode terminals, and determining a value of a second electrical reactance of the liquid sample bridging the spacing for the given frequency. The method may include generating a value representing the concentration of glycated haemoglobin (HbA1c) in the blood within the sample according to the first electrical reactance value, the second electrical reactance value and a value of the relative volume of red blood cells in the liquid sample (haematocrit). The given frequency preferably has a value in the range 500 KHz to 1.5 MHz, e.g. about 1 MHz. More preferably, the given frequency has a value in the range 750 KHz to 1.25 MHz, yet more preferably the given frequency has a value in the range 850 KHz to 1.15 MHz, even more preferably the given frequency has a value in the range 900 KHz to 1.1 MHz, yet even more the given frequency has a value in the range 970 KHz to 1.03 MHz.

In a fifth aspect, the invention may provide a sample measurement method for performing electrical measurements on a liquid sample containing blood, the method comprising receiving the liquid sample on a sample plate comprising electrode terminals which are separated by a spacing adapted to be bridged by blood from the liquid sample, and applying to the electrodes an alternating electrical current having a first signal frequency to generate a first alternating potential difference across the spacing between the electrode terminals. This method may include determining a value of a first electrical resistance of the liquid sample bridging the spacing for the first signal frequency. The method may include applying to the electrodes an alternating electrical current having a second signal frequency exceeding the first signal frequency to generate a second alternating potential difference across the spacing between the electrode terminals, and determining a value of a second electrical resistance and a value of a reactance of the liquid sample bridging the spacing for the second signal frequency. This method may include generating a value for the relative volume of red blood cells (haematocrit) in the liquid sample according to the first electrical impedance value and the second electrical impedance value. The first frequency preferably has a value in the range 1 KHz to 150 KHz, e.g. about 50 KHz. More preferably, the first frequency has a value in the range 25 KHz to 125 KHz, yet more preferably the first frequency has a value in the range 35 KHz to 100 KHz, even more preferably the first frequency has a value in the range 45 KHz to 75 KHz, yet even more the first frequency has a value in the range 47 KHz to 53 KHz. The second frequency preferably has a value in the range 500 KHz to 1.5 MHz, e.g. about 1 MHz. More preferably, the second frequency has a value in the range 750 KHz to 1.25 MHz, yet more preferably the second frequency has a value in the range 850 KHz to 1.15 MHz, even more preferably the second frequency has a value in the range 900 KHz to 1.1 MHz, yet even more the second frequency has a value in the range 970 KHz to 1.03 MHz.

The invention in its fourth aspect may comprise generating a value representing the concentration of glycated haemoglobin (HbA1c) in the blood within the sample using the value representing the relative volume of red blood cells in the liquid sample (haematocrit) as generated according to the invention in its fifth aspect.

BRIEF DESCRIPTION OF THE SEVERAL VIEWS OF THE DRAWINGS

To better illustrate the invention there now follows a non-limiting examples of embodiments of the invention with reference to the accompanying drawings of which.

DETAILED DESCRIPTION OF THE INVENTION

Figure 1:
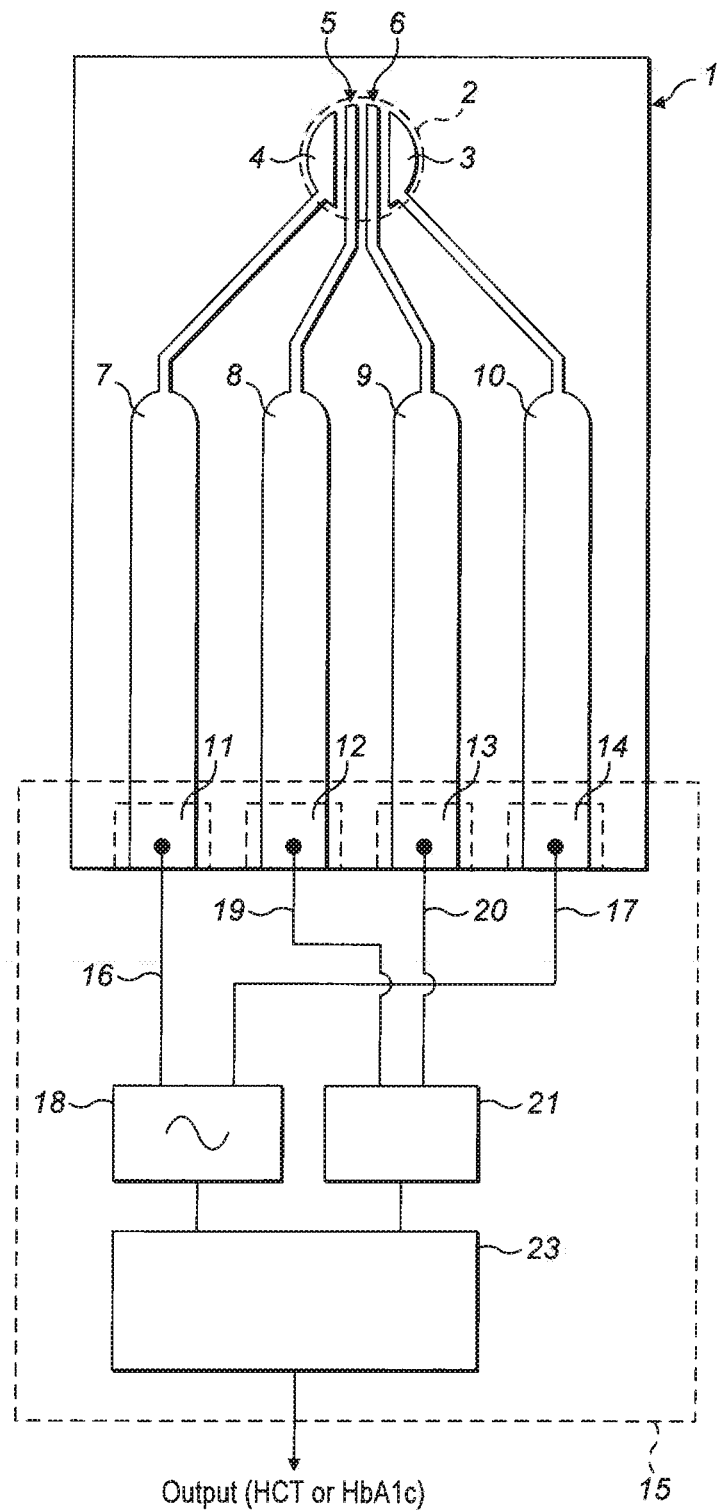
FIG. 1 illustrates schematically a sampling plate attached to a sampling unit.

In the drawings, like items are assigned like reference symbols.

FIG. 1 shows a sampling plate (1) in the form of a strip of firm and non-conductive material (e.g. plastic) possessing a circular sample zone (2) defined by a circular recess formed within the strip for receiving a liquid blood sample. Within the sample zone there are four electrode terminals (3, 4, 5, 6) formed upon a surface of the plate forming the floor of the sample zone and exposed for contact with a received sample. The electrode terminals each comprise a layer of inert conductive material, preferably Gold.

The four electrode terminals comprise two drive electrode terminals (3, 4) each of which is in the shape of a circular segment the curved edge of which coincides with a part of the circular edge of the circular sample zone. The straight segment edge of each one of the two drive electrode terminals is parallel to and opposes the straight segment edge of the other of the two drive electrode terminals to define between them a straight, elongate drive gap of uniform width within the sample zone across which the drive electrode terminals oppose each other and across which a drive current is driven as explained in more detail below.

Within the elongate drive gap extend two straight parallel sensing electrode terminals (5, 6) in the form of two strips separated from each other by a sensing gap of uniform width defined by the spacing between opposing side edges of each strip. The opposing edges of the two sensing electrodes are substantially parallel to each straight segment edge of each of the two drive electrode terminals.

Furthermore, the straight segment edge of each one of the two drive electrode terminals (3, 4) opposes a correspondingly straight and parallel edge of an adjacent sensing electrode terminal (6, 5) to define therebetween a substantially straight and elongate partitioning gap which extends along the sample zone in parallel to the sensing gap. Thus, the two sensing electrodes define a straight and uniform sensing gap of receiving parts of the blood sample within the sensing zone, and the two drive electrode terminals define, together with neighbouring sensing electrode terminals, two partitioning gaps either side of the sending electrodes which are parallel to each other and to the sensing gap, and which separate the sensing electrode terminals from the drive electrode terminals within the sensing zone.

The width of the sensing gap is preferably between about 90 microns and about 150 microns, for example about 100 microns and is dimensioned to admit, at any point along the sensing gap, a single human blood cell without permitting that blood cell to bridge the gap and concurrently contact both of the two sensing electrodes defining the sensing gap. Rather, the gap is dimensioned to allow a blood cell space to oscillate within the gap between the opposing sensing electrodes in response to an alternating current driven transversely across the sensing gap between the two drive electrode terminals (3, 4). In this way, a row of blood cells may be arranged along the sensing gap when a liquid blood sample is received within the sensing zone and may be subject to an alternating drive current directed transversely (e.g. substantially perpendicular) to the row of cells.

This geometry, and the linear array of single blood cells it enables in use, has been found to provide a surprisingly accurate and stable means of measuring not only haematocrit (HCT) values for the blood sample, but also has been found to enable accurate measurement of the concentration of glycated haemoglobin in the blood sample (i.e. the so-called "fixed" glucose level within blood cells, or the so-called HbA1c value). Accurate determination of the former has been found to be important for enabling accurate determination of the latter—i.e. one needs to know how much of the sample is comprised of red blood cells in order to be able to determine the quantity of fixed glucose they carry. The present invention could be implemented to do both simultaneously or sequentially with reliability and accuracy.

The width of each of the two parallel partitioning gaps, either side of the sensing electrode terminals is preferably about 1.5 times the value of the width of the sensing gap. Again, this gap dimension and the parallel arrangement of blood cells the partitioning gaps enable, has been found to assist in providing accuracy and stability.

Each of the electrode terminals within the sensing zone is electrically connected to a respective electrical conductor line formed within the body of the sensing plate so as to be electrically insulated along its length until terminating at an exposed electrical contact zone at an end or side of the sampling plate distal from the sample zone. For example, the first drive electrode terminal (3) is electrically connected to a first drive contact zone (14) via a first (10) electrical conductor strip (e.g. Gold). The first sensing electrode terminal (6) is electrically connected to a first sensing contact zone (13) via a second (9) electrical conductor strip (e.g. Gold). Similarly, the second sensor electrode terminal (5) is electrically connected to a second sensing contact zone (12) via a third (8) electrical conductor strip (e.g. Gold). Finally, the second drive electrode terminal (4) is electrically connected to a second drive contact zone (11) via a fourth (7) electrical conductor strip (e.g. Gold).

These four contact zones are arrayed in a line along an edge of the sensing plate, at the distal end of the strip, to permit the end of the strip to be inserted into an electrical socket/port of an electrical sensing unit (15) to place the each one of the four contact zones simultaneously in electrical connection with a respective one of four (16, 17, 19, 20) electrical contact terminals of the sensing unit.

The sensing unit may be a handset, or part of a larger piece of equipment. The sensing unit comprises an alternating current source (18) arranged to generate an alternating electrical current of selected amplitude and selected frequency, and apply the alternating current to a first and second sensing contact terminals (16, 17) for application to the drive electrode terminals (3, 4) as a drive current via the first and second drive contact zones of the sensing plate. A control processor unit (23) is operatively connected to the current source (18) to control the frequency of the generated current signal. For example, the control processor may control the current signal frequency to be a value (e.g. 50 KHz) within a first continuous range of values from about 1 KHz to about 150 KHz, or to be a value (e.g. 1 MHz) within a second continuous range of values from about 500 KHz to about 1.5 MHz. The control processor is arranged to selectively switch the frequency value from a first value within the first range to a second value within the second range.

A detector unit (21) is electrically connected to a first and second contact terminals (19, 20) for receiving voltage signals from the first and second sensing electrodes (6, 5) via the first and second sensing contact zones of the sensing plate.

The control processor (23) is arranged to control the electrical current generator to apply an alternating electrical current at a first frequency (selected from within the first range of values) and concurrently to control the voltage detector (21) to measure a first voltage signal received via the first sensing electrode and to measure a second voltage signal received via the second sensing electrode. Subsequently, the control processor further controls the electrical current generator to apply an alternating electrical current at a second frequency exceeding the first frequency (selected from the second frequency range) and concurrently to control the voltage detector (21) to measure a third and a fourth voltage signal value received from the first and second sensing electrodes respectively.

The control processor is arranged to calculate a first electrical resistance value ($R_1$, Ohms) using an amplitude of the voltage difference between the first and second voltages measured at the first frequency and the amplitude of the associated applied alternating current, and to calculate an electrical impedance value ($Z_2 = R_2 \pm jX_3$, Ohms) using an amplitude of the voltage difference between the third and fourth voltages measured at the second frequency, and the amplitude of the associated applied alternating current. Here R represents a resistive component of impedance and X represents a reactive component of impedance. The quantity $j = \sqrt{-1}$.

Using these two impedance values, the control processor is arranged to generate a value (HCT) representing the relative volume of red blood cells in the liquid sample (haematocrit) according to the following equation.

$$HCT = \left[ A\ln\left(\frac{R_1}{R_2}\right) + B\ln(X_3 + X_0) - C \right]$$

This equation is discussed in more detail below (Equation (3)). The values of the constants A, B, C and $X_0$ may be determined for a given sensing gap and/or partitioning gap width, and electrode structure/material for a given sensing plate, by routine calibration and experimentation as would be readily apparent to the skilled person. It will be appreciated that HCT values of calibrated blood samples may be obtained via other known methods to enable such calibration. Using this method the standard error of the estimated HCT values, when compared against the known micro-haematocrit method, is found to be less than 1.5% when measuring HCT in the range of 20 to 60%.

In a modified version of the embodiment of FIG. 1, one drive electrode (4) of the electrodes in the sampling zone (2) may possess a deposit of an enzyme (e.g. glucose oxidase, glucose dehydrogenase) to react with free glucose in the plasma component of the blood sample to substantially oxidise it. In that case the control processor is arranged to control the electrical current generator to apply an alternating electrical current at a first frequency (selected from within the second range of values) with a DC voltage offset (e.g. about 0.25 volts) applied across the drive electrodes (3, 4) and concurrently to control the voltage detector (21) to measure a first voltage signal received via the first sensing electrode, and to measure a second voltage signal received via the second sensing electrode. Subsequently, the control processor further controls the electrical current generator to apply an alternating electrical current at the same first frequency (selected from the second frequency range) without a DC voltage offset applied across the drive electrodes and concurrently to control the voltage detector (21) to measure a third and a fourth voltage signal value received from the first and second sensing electrodes respectively.

The control processor is arranged to calculate a first electrical reactance value ($X_1$, Ohms) using an amplitude of the voltage difference between the first and second voltages measured at the first frequency and the amplitude of the associated applied alternating current, and to calculate a second electrical reactance value ($X_2$, Ohms) using an amplitude of the voltage difference between the third and fourth voltages measured at the second frequency, and the amplitude of the associated applied alternating current.

The control processor then calculates a value (HbA1c) representing the concentration of glycated haemoglobin within the blood sample according to the following equation.

$$HbA1c = 100 \times \left(1 - \frac{X_1}{HCT \times X_2}\right)$$

Where HCT is a predetermined haematocrit value for the blood sample obtained independently, e.g. according to the invention, or otherwise.

This method has been found to provide an HbA1c measurement result with an accuracy of ±10% or better within 20 seconds. The concentration of HbA1c depends on both the concentration of glucose in the blood and the lifespan of the erythrocyte (the haemoglobin cell). Because erythrocytes are in circulation for approximately 120 days HbA1c represents the integrated glucose concentration over the preceeding 8 to 10 weeks, which is therefore free of the large fluctuations that occur daily in blood glucose concentrations in blood plasma.

Before measurement of a sample of blood is performed, the temperature of the sampling plate is established. This may be done by any suitable means such as would be available and apparent to the skilled person. Preferably, the temperature of the sampling plate may be determined means of a thermocouple mounted in the strip port connector. To further improve accuracy the temperature of the sample should preferably be maintained at 37° C.±1.5° C. This may be achieved, for example, by environmental temperature control of the area in which sampling plates are stored or used, or by means of a heater (e.g. trace heating, Ohmic heating wire/strip etc, not shown) formed in the strip electrically connectable to a power source within the sensing unit (15, FIG. 1) to controllably heat the sampling plate. A thermocouple (not shown) may also be formed within/upon the sampling plate, also being arranged to be powered by the sampling unit when the sampling plate is connected thereto in use. This may be used to regulate the heater (if present) and/or simply to allow the sampling unit to determine the temperature of the sampling plate.

It will be noted that both the reactive ($X_3$) and resistive ($R_2$) components of the impedance value ($Z_2$) are employed in these equations when employing the higher frequency AC signals, whereas only a resistive component ($R_1$) is used at lower signal frequencies. This stems from a consideration of the electrical current paths which may be considered to flow across the linear arrays of blood in the sample received within the sampling and partitioning gaps of the sample zone as follows.

Figure 5:
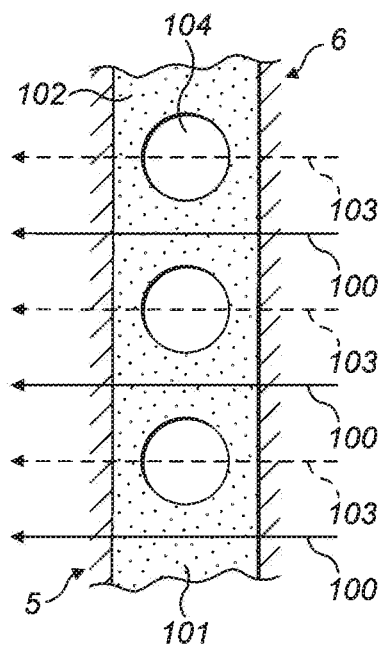
FIG. 5 schematically illustrates equivalent circuit diagrams.
Figure 5:
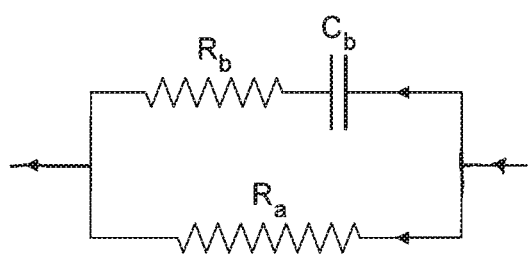

FIG. 5 illustrates an equivalent circuit representing what is postulated to be the conductive pathways for electrical current driven through a blood sample between drive electrodes of the sampling plate. This is postulated, but not asserted, as it is useful to understanding.

A first current pathway (100) passes current across the line of blood cells (101) within the sensing gap through the blood plasma (102), or other added liquid, between blood cells. This conductive path can be considered as purely resistive in nature. A second conductive path (103) passes through a blood cell (104). The path through the contents of the blood cell (e.g. any glucose) may be considered as resistive, whereas the path through the walls of the blood cell may be considered capacitive.

These two current pathways act in parallel and present an electrical impedance (Z) which may be approximated as follows.

$$Z = R + jX = R_a \left\{ \frac{1 + \omega^2 C_b^2 R_b (R_b + R_a) - j\omega C_b R_a}{1 + \omega^2 C_b^2 (R_b + R_a)^2} \right\}$$

Where $R_a$ is the resistance of the plasma, $R_b$ is the resistance of the contents of the blood cell including any glucose, and $C_b$ is the capacitance of the blood cell, where $j=\sqrt{-1}$.

At sufficiently low frequencies, the reactive impedance of the blood cell, arising from the capacitance of the blood cell, is very high and prevents current flow through the cell. Substantially only the first current path (through plasma) is available. At sufficiently high frequencies, the reactive impedance of the blood cell falls and the second current pathway becomes increasingly significant. The second pathway brings the influence of the resistance of the content of a blood cell to bear on the value of the impedance Z as well as the remaining influence of the plasma due to the remaining first current pathway. In this way, employing the components of impedances of a blood sample at both low and high frequencies enables the influence of the contents of the blood cell to be probed.

It has been found that the presence of glucose within a blood cell has a measurable effect upon the phase of the electrical current signal passing through the sample. It is postulated that this may be because the presence of glucose within the blood cell increases the number of electrons available to react to the oscillating drive signal thereby increasing the flow of current through the cell. This influences the phase of the current passing through the sample. The presence of glucose in the cell can be considered as influencing the resistance $R_b$ of the cell contents, according to the equivalent circuit model. The phase of a voltage sensed in the blood sample under such circumstances could be represented as:

$$\text{Phase} = \arctan\left(\frac{X}{R}\right) = \arctan\left(\frac{\omega C_b R_a}{1 + \omega^2 C_b^2 R_b (R_b + R_a)}\right)$$

The phase angle can be seen to be influenced by $R_b$, the resistance of the cell contents. Thus, it is postulated that this may be part of the origin of the relationship between the phase of an electrical drive signal within the sample, and the amount of glucose within the blood cells (i.e. relating to HbA1c).

Figure 2:
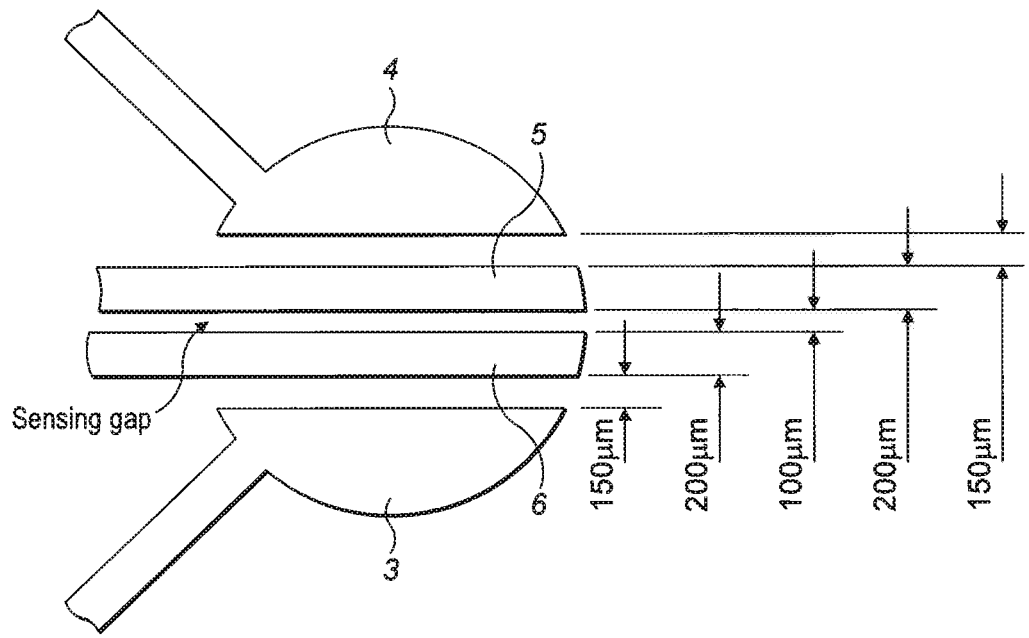
FIG. 2 illustrates the electrode terminals of the sampling plate in more detail.
Figure 3:
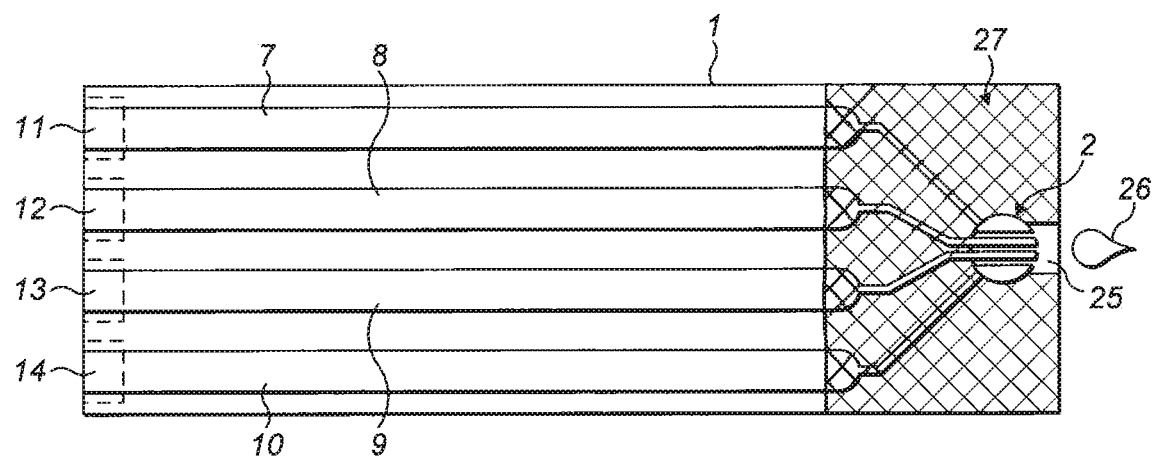
FIG. 3 illustrates the sampling plate in isolation, in the form of a disposable sampling strip.
Figure 4:
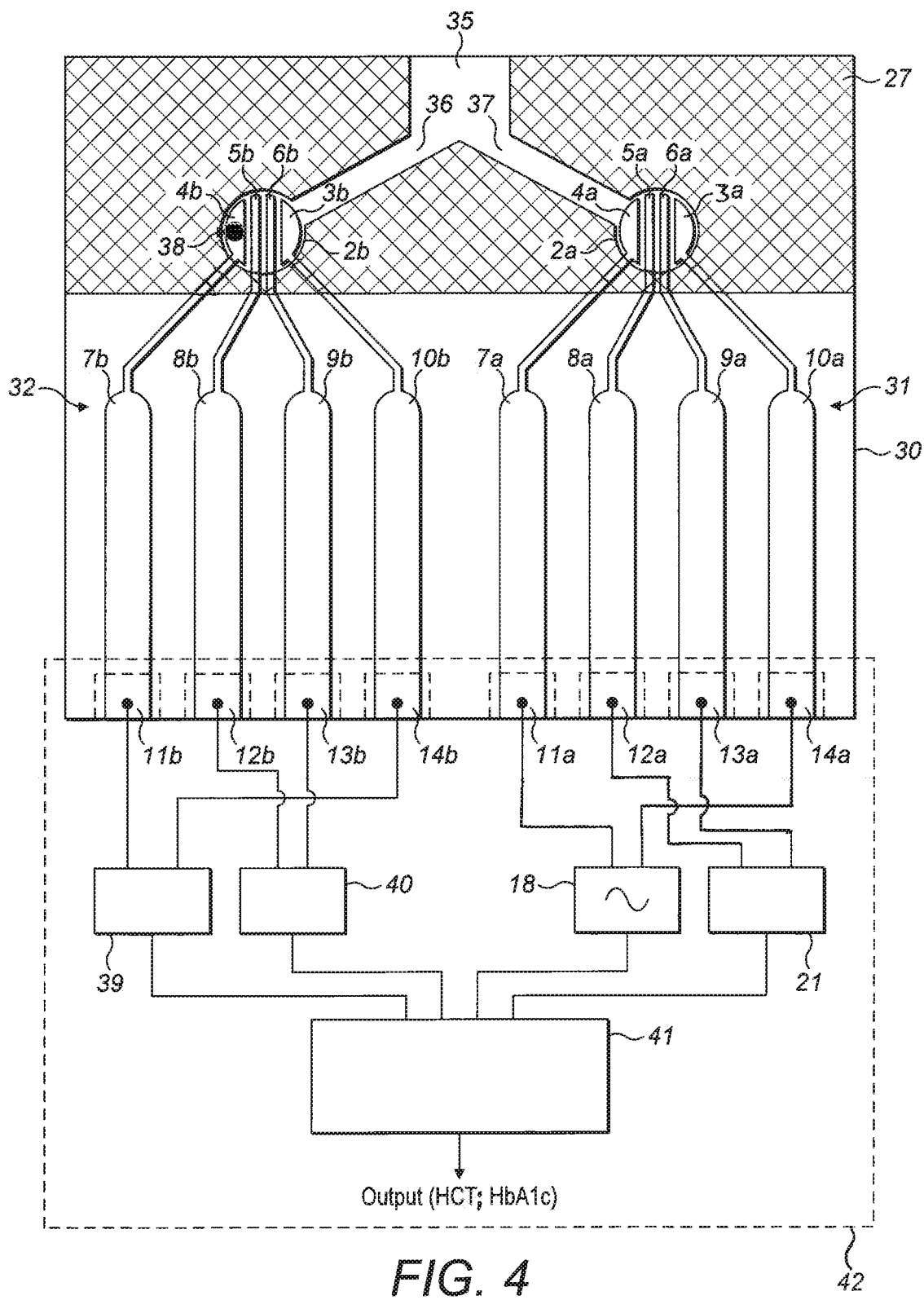
FIG. 4 illustrates schematically a sampling plate and sampling apparatus according to another embodiment of the invention, comprising two sample zones and electrode groupings.

FIG. 2 illustrates a close-up view of the electrode terminals (3, 4, 5 and 6) of FIGS. 1, 3 and 4. The figure indicates a suitable sensing gap width and partitioning gap widths either side of the sensing gap. A sensing gap of 100 microns uniform in width is suitable. Partitioning gap widths of 150 microns is also suitable. Each sensing electrode terminal within the drive gap, between the two drive electrode terminals (3, 4) is a straight-edged flat strip of Gold having a substantially uniform width of 200 microns. This results in a drive gap width of 800 microns. Similarly, each drive electrode terminal is a flat segment of Gold.

FIG. 3 illustrates an embodiment of a sensing plate of FIG. 1 in the form of a disposable strip (1). The electrode and conductor structure of the disposable strip is as described above with reference to FIG. 1. In addition, the end of the strip containing the drive and sensing electrode terminals (3, 4, 5 and 6) comprises sample zone (2) for receiving the blood sample, surrounded by an air-porous body (27) which is in fluid communication with the sample zone wherein the air porous body is arranged to receive air displaced from the sample zone as the liquid blood sample is received into the sample zone.

"In fluid communication with" may mean interfacing, where "interfacing" means sharing a common boundary. Preferably "in fluid communication with" refers to where the air porous body is adjacent to the sample zone. The air porous body may define a floor of the sample zone and/or wall(s) of the sample zone. The air porous body may surround the sample zone. Preferably the air porous body defines the sample zone, or defines an outer boundary of the sample zone. Preferably the air porous body defines the perimeter of the sample zone or at least part of the perimeter of the sample zone. Preferably the air porous body is external to the sample zone itself. Preferably the sample zone is free of air porous body.

Preferably the air porous body is arranged to receive displaced air as the liquid sample approaches the air porous body. Preferably the air porous body is arranged to receive air displaced in the same direction as the liquid sample travels (or spreads) into the sample zone. Preferably the air porous body is arranged to receive a side-ways displacement of air as the liquid sample approaches the air porous body in a side-ways manner. Preferably the sample zone is arranged to prevent back flow of the liquid sample.

An advantage of this arrangement is that the air porous body helps the liquid sample to flow into the sample zone with minimal air resistance, by providing a means by which air can be directly displaced—preferably in the same direction as the liquid sample enters the sample zone. This permits the liquid sample to enter the sample zone at a faster rate. In contrast, where such an air porous body is absent, air resistance retards the flow of the liquid sample into the sample zone.

Another advantage of the arrangement is that the air porous body helps the liquid sample to spread uniformly throughout the sample zone, thus giving greater sampling consistency and consequently more accurate measurements. In contrast, where the air porous body is absent, air resistance affects the fluid dynamics of the liquid sample by discouraging spreading (air resistance from all sides) and instead encouraging the liquid sample to remain collectively associated as a bulk (aided by surface tension). As such the liquid sample tends to flow as a bulk in a single direction since in this way the bulk overcomes air resistance in that particular direction. Another advantage is that formation of air-pockets is alleviated, which again allows for better spreading and more accurate measurements. The liquid sample is preferably hydrophilic, more preferably aqueous-based, and most preferably blood. In this case, blood glucose levels of a diabetic patient may be measured. The air porous body is preferably substantially impermeable to the liquid sample. The air porous body is preferably substantially impermeable to water. The air porous body is preferably substantially impermeable to an aqueous liquid sample, and most preferably substantially impermeable to blood.

The air porous body is preferably located substantially around the perimeter of the sample zone. Preferably a floor of the sample zone is free of air porous body. Preferably the sample zone is free of a roof. Where the sample zone comprises a roof, the roof is preferably free of air porous body. The air porous body preferably comprises hydrophobic material. Preferably the air porous body comprises at least 50 wt %, more preferably at least 70 wt %, and most preferably at least 90 wt % hydrophobic material. The air porous body preferably has an average pore size between 10 and 300 microns, preferably between 50 and 200 microns, and most preferably between 100 and 150 microns. The air porous body preferably comprises an air porous mesh, which again is preferably hydrophobic overall. Such an air porous mesh preferably comprises polyether ether ketone (PEEK), polypropylene (PP), polyester (PET), polyvinylidene fluoride (PVDF), ethylene chlorotrifluoroethylene (ECTFE), ethylene co-tetrafluoroethylene (ETFE), nylon (polyamide), or fluorinated ethylene-propylene (FEP). The air porous mesh preferably comprises polyester (PET). Most preferably the air porous mesh comprises Sefar 07-120 34.

Accordingly, where the sample zone (2) has a roof, the sample zone is accessible via an entry port (25) into which a blood sample (26) may be placed. By capillary action, the blood sample is drawn through the entry port and into the sampling zone, displacing air into the air-porous body (27) as it does so, to finally occupy the sample zone covering the drive and sensing electrode terminals there. A breathable structure created beneath a thin polymer film covering the sample zone, as a roof. Typically the porous layer is a mesh made up of strands of polymer that are coated to create a hydrophobic boundary to the blood as it flows on to the sample zone. A geometric shape cut into the mesh defines the sample zone and entry port which allows the sample to fill the sample zone under capillary action created by the thin top film.

FIG. 4 illustrates a further embodiment of the invention in which a sampling plate (30) comprises two sets (31, 32) of substantially identical drive electrode and sensing electrode arrangements each being substantially identical in structure as the electrode and conductor structure described above with reference to FIGS. 1 to 3. In particular, a first electrode group (31) comprises a pair of aforesaid drive electrode terminals (3a, 4a) located within a first sample zone (2a) of the sampling plate. A pair of aforesaid sensing electrode terminals (5a, 6a) extend in parallel along the drive gap formed between the two drive electrodes. A respective one of four conductive strips (7a, 8a, 9a, 10a) electrically connects a drive terminal or sensing electrode terminal to a respective one of four separate contact zones (11a, 12a, 13a, 14a) arranged along the distal edge of the strip. A second electrode group (32) comprises a pair of aforesaid drive electrode terminals (3b, 4b) located within a second sample zone (2b) of the sampling plate. A pair of aforesaid sensing electrode terminals (5b, 6b) extend in parallel along the drive gap formed between the two drive electrodes. A respective one of four conductive strips (7b, 8b, 9b, 10b) electrically connects a drive terminal or sensing electrode terminal to a respective one of four separate contact zones (11b, 12b, 13b, 14) arranged along the distal edge of the strip. Accordingly, eight contact zones arrayed along the distal edge of the sampling strip for insertion into a socket/port of an electrical sensing unit (42) to place the each one of the eight contact zones simultaneously in electrical connection with a respective one of eight electrical contact terminals of the sensing unit.

The first and second sample zones (2a, 2b) of the sampling plate are each in communication with a common single sample entry port (35) via a respective one of two sample conduits (36, 37) which bifurcate from the entry port and communicate with a given sample zone. The two sample zones (2a, 2b) are each surrounded by an air-porous body (27), as described above, which is in fluid communication with each of the sample zones wherein the air porous body is arranged to receive air displaced from the sample zone as the liquid blood sample is received into the sample zone. The air porous body defines the entry port (35) and the sample conduits (36, 37) as well as the circular periphery of each of the two sample zones.

A quantity of an enzyme (38), (e.g. glucose oxidaze ("GOX") or glucose dehydrogenase (GDH)), is located upon one of the two drive electrode terminals (4b) in the second sample zone (2b). The enzyme (e.g. GOX or GDH) is placed to allow it to make contact with, and react with, a blood sample entered into the second sample zone. In doing so, the enzyme reacts with the blood sample to consume any free glucose present within the plasma of the blood sample. As a result, one the reaction has completed, the blood sample located within the second sample zone contains substantially no free glucose, and any glucose present should be substantially only fixed glucose within the red blood cells of the blood sample which is inaccessible to the enzyme (e.g. GOX or GDH).

In the sensing unit (42), a control processor (41) is arranged to control the current source (18) and the voltage detector unit (21) as described above with reference to FIG. 1 when measuring haematocrit (HCT). The control processor (41) is arranged to control a second current source (39) and a second voltage detector unit (40) of the sensing unit, as described above with reference to FIG. 1 ("modified version") when used to measure HbA1c.

Figure 6:
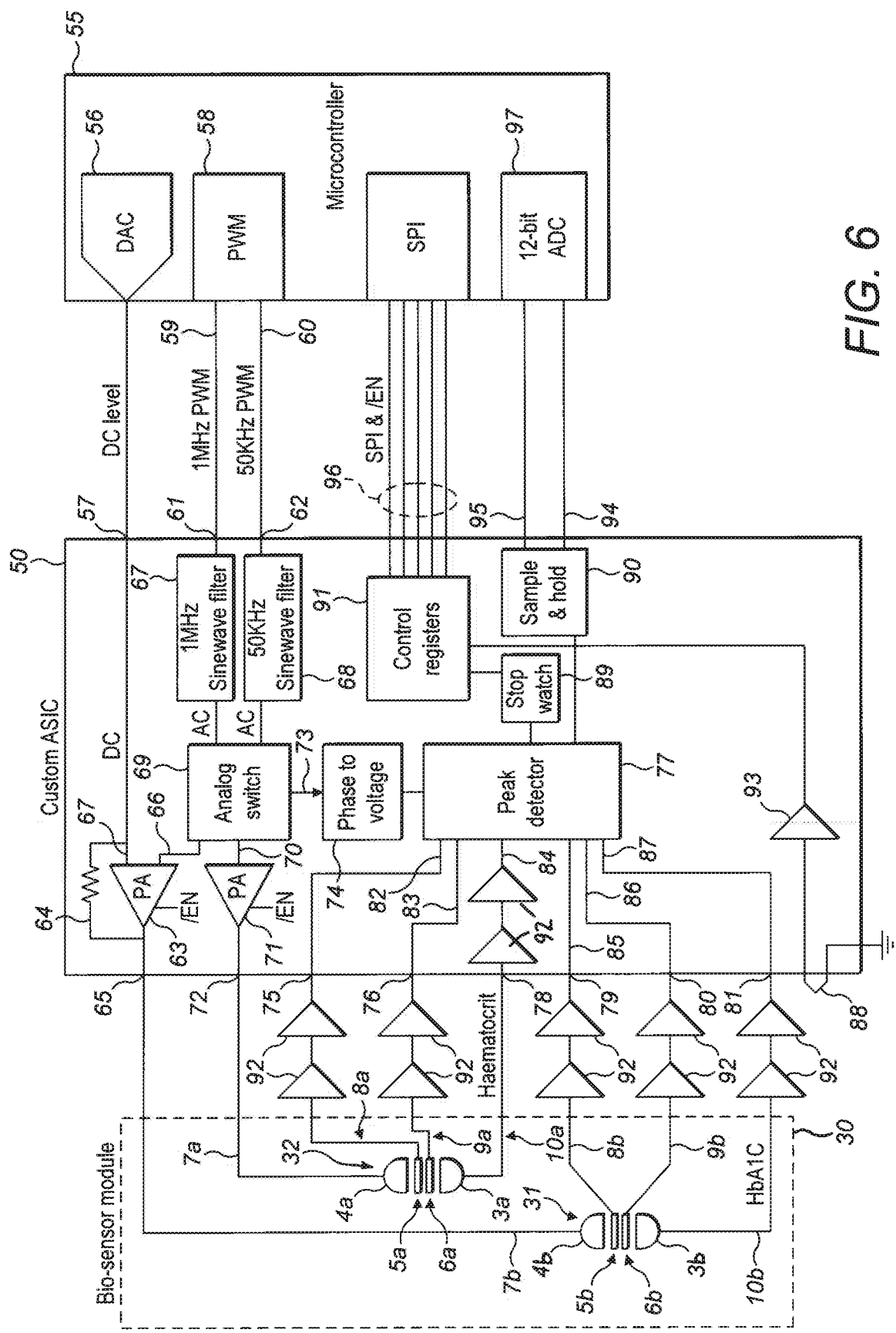
FIG. 6 schematically shows a sampling plate and sampling unit containing an ASIC comprising circuitry components adapted to implement signal generation and reception to and from a sampling plate.

FIG. 6 schematically illustrates an ASIC (application specific integrated circuit, 50) arranged for connection to a microcontroller (55) integrated circuit for use within the sensing unit (42, FIG. 4). The ASIC is responsive to the control signals from a control unit (55) to apply to the second group of electrodes (31) of the sensing strip an alternating (AC) current having a first frequency of 1 MHz and to selectively apply a direct voltage (DC) of most preferably a substantially constant value concurrently, accordingly to the control signals. This is for the purposes of measuring HbA1c in the blood sample bridging the electrodes of that second group.

The ASIC is responsive to the control signals from a control unit (55) selectively to apply to the first group of electrodes (32) of the sensing strip an alternating (AC) current having either a first frequency of 1 MHz or second frequency of 50 KHz according to the control signals. This is for the purposes of measuring haematocrit in the blood sample bridging the electrodes of that second group.

The ASIC is arranged to receive voltage signals from the first and second sensing electrode terminals (5b, 6b) of the second group of electrodes (31) of the sensing plate, and to receive voltage signals from the first and second sensing electrode terminals (5a, 6a) of the first group of electrodes (32) of the sensing plate. The ASIC is responsive to the voltage signals and the current signals to measure peak/amplitude values for those voltages and currents for use by the microcontroller in calculating electrical resistance and reactance values of blood samples bridging the electrodes of the first and second electrode groups (31, 32) to determine values of haematocrit and HbA1c therein.

The control unit (55) performed the functions of the control processor unit (41) of FIG. 4.

In particular, the microcontroller (55) is arranged to provide a direct (DC) voltage level (most preferably a substantially constant (DC) voltage level) and to output a corresponding (DC) analogue output signal via a digital-to-analogue converter output (56) connected to an input port (57) of the ASIC (50). Furthermore, the microcontroller is also arranged to produce an alternating (AC) pulse-width modulated square-wave analogue output signal via a pulse-width modulator (PWM, 58) as a first signal (59) having a frequency of 1 MHz and to input the signal to a second input port (61) of the ASIC, and to produce a second separate modulated square-wave output signal (60) having a frequency of 50 KHz and to input the signal to a third input port (62) of the ASIC. These two pulse-width modulated output signals are electrical current signals which are each maintained at a predetermined amplitude level (most preferably substantially constant) by the microcontroller. The ASIC includes a first pre-amplifier in the form of an operational amplifier (63) comprising a feed-back loop (64) including a resistor. The pre-amplifier is arranged to receive the DC voltage signal from the microcontroller at a first input port (67) of the pre-amplifier, and to output an amplified value to a first output port (65) of the ASIC. The ASIC also includes a 1 MHz sinewave filter unit (67) and a 50 KHz sinewave filter unit (68) each arranged for receiving and filtering a respective 1 MHz and a 50 KHz oscillating current signal input from the microcontroller at the second and third input ports (61, 62) of the ASIC. Each of the sinewave filter units is arranged to receive the respective square-wave (PWM) signal input to it, and to alter the square-wave shape of the signal into substantially a sine-wave shape and to output the result as an AC sine-wave signal. An analogue switch unit (69) is provided in the ASIC and has two input ports for receiving a respective one of the two AC sinewave signals output from the 1 MHz and 50 KHz sinewave filter units. The analogue switch unit is arranged to be controlled by the microcontroller to output selectively one of the 1 MHz sinewave (AC) signal and the 50 KHz sinewave signal to a signal input port of a second pre-amplifier (71) in the ASIC for amplifying that output signal. In this way the microcontroller is able to control, via the analogue switch unit, which of the 1 MHz and the 50 KHz sinewave (AC) signals is ultimately output from the second pre-amplifier and from the ASIC.

The sampling strip (30) is shown as electrically connected to the ASIC of the sensing unit such that a first drive electrode terminal (4b) of a second group of electrodes (31) for sensing HbA1c, is electrically connected to the first output port of the ASIC, and such that a first drive electrode terminal (4a) of a first group of electrodes (32) for sensing haematocrit, is electrically connected to the second output port of the ASIC.

In addition, the analogue switch unit is arranged to be controlled by the microcontroller to output the 1 MHz sinewave (AC) signal to a second signal input port (66) of the first pre-amplifier (63) in the ASIC for amplifying that output signal. The first pre-amplifier unit is arranged to selectively amplify a 1 MHz sinewave (AC) signal either with or without the concurrent presence of the DC voltage level applied to the first input port (67) of that amplifier. The microcontroller controls when/if the DC voltage level is applied to the first pre-amplifier unit.

The analogue switch unit is further arranged to output, via a third output port (73), a signal which is representative of the time of a peak/amplitude of the AC sinewave signal received by the analogue switch unit from either of the first and second sinewave filter units. This signal is input to a phase-to-voltage unit (74) which, as shall be explained in more detail below, is arranged to measure a temporal phase difference between an AC current applied to the drive electrodes of the first and second groups of electrodes, and an AC voltage generated between sensing electrode terminals of the respective groups of electrodes of the sensing plate, and to generate the result as a signal representative of that temporal phase difference.

The ASIC includes a peak detector unit (77) in communication with the phase-to-voltage unit and comprising a first and second signal input ports (82, 83) in communication with first and second voltage input ports (75, 76), respectively, of the ASIC for receiving voltage signals from the sensing electrode terminals (5a, 6a) of the first group of electrodes (32) of the sensing plate. A third input port (84) of the peak detector unit is arranged in communication with a second drive electrode (3a) of the first group of drive electrodes (32) via a first current input port (78) of the ASIC and is arranged to receive the current driven through the first group of electrodes between the first drive electrode (4a) and the second drive electrode (3a) of that group.

The peak detector unit also comprises a fourth and fifth signal input ports (85, 86) in communication with third and fourth voltage input ports (79, 80), respectively, of the ASIC for receiving signals from the sensing electrode terminals (5b, 6b) of the first group of electrodes (31) of the sensing plate. A sixth input port (87) of the peak detector unit is arranged in communication with a second drive electrode (3b) of the first group of drive electrodes (31) via a second current input port (81) of the ASIC and is arranged to receive the current driven through the second group of electrodes between the first drive electrode (4b) and the second drive electrode (3b) of that group.

Thus, the ASIC includes a first (75) and second (76) voltage input ports which connect electrically to a first (82) and second (83) input ports of a peak detector unit and are adapted for receiving a respective first and second voltages from respective of the sensing electrodes of the first group of electrodes (32). The ASIC also includes a third and fourth voltage input ports (79, 80) which are similarly electrically connected to input ports (85, 86) of the peak detector unit. A first current input port (78) and a second current input port (81) are each respectively connected to first and second current input ports (84, 87) of the peak detector unit. Each of the first to sixth input ports of the peak detector unit are arranged to receive respective voltage and current signals which are amplified by a respective pair of amplifier units (92) within the apparatus, arranged in series electrical connection along the respective signal transmission line leading to the input ports in question. These amplifier units serve to amplify the respective signals prior to receipt by the peak detector unit, and may be formed in the ASIC if desired, or elsewhere in the sensing unit but operably connected to the ASIC as shown in the Figures.

The peak detector unit comprises an output port electrically connected to a sample-and-hold unit (90) which is arranged to receive from the peak detector unit a signal representing a value of the peak in an AC voltage signal received by the peak detector, and/or a value representing a peak current value received by the peak detector. These peak values generally represent amplitude values of an associated AC current and voltage signal inputs to the peak detector unit from the electrodes of the sampling plate (bio-sensor module). The sample-and-hold unit is operable to momentarily retain signal values received from the peak detector unit as and when required for subsequent transmission to the microcontroller.

The phase-to-voltage unit (74) possesses an output port electrically connected to an output port of the ASIC for outputting a voltage signal representing a measured phase difference (measured time shift) between the peak voltage values detected by the peak detector, and the peak values of the AC current signal output by the analogue switching unit.

A stop-watch unit (89) is operably connected to and controlled by the microcontroller (55) via the control register unit (91) and the interface (SPI) with the microcontroller. The stop-watch unit is arranged to measure a time interval between detected signal peaks detected by the peak detector unit for use in measuring a phase angle between applied current and measured voltage.

In this way, the phase-to-voltage unit and the peak detector unit provide values representing an amplitude of an AC voltage signal and an AC current signal received by the peak detector unit, and a phase difference incurred between those signals. With these measured values, the microcontroller is arranged to calculate values of resistance and reactance of samples within the sampling zones of the sampling plate (bio-sensor module).

The sample and hold unit (90) has two output ports each in communication with a respective first and second output port (94, 95) of the ASIC for separately outputting values associated with the first and second groups of electrodes (31, 32) respectively.

The voltage output port of the ASIC is arranged to be connectable (and is shown as connected to) a biosensor module in the form of a sampling strip such as is shown in FIG. 4. The first current output port (65) of the ASIC is connected to a drive electrode (4b) in the sampling zone of the sampling strip dedicated to measuring HbA1c and the second current input port (81) is arranged to be electrically connected to (and is shown as connected) to the other drive electrode (3b) in that sampling zone. Similarly, the second current output port (72) of the ASIC is electrically connectable to (and shown as connected) a first drive electrode (4a) in the other sampling zone of the sampling strip dedicated to measuring haematocrit, whereas the other drive electrode (3a) in that sampling zone is electrically connectable to (as is shown as connected) the first current input port (78) of the ASIC.

The two sensing electrodes (5a, 6a) of the sampling strip within the sampling zone for haematocrit are each separately connected to the first and second voltage input ports (75, 76), respectively, of the ASIC via a respective pair of amplifier units (92). Similarly, the two sensing electrodes (5b, 6b) in the sampling zone of the sampling strip dedicated to measurement of HbA1c are each separately connected to a respective one of the third and fourth voltage input ports (79, 80) of the ASIC. In this way, electrical currents may be driven across the drive electrodes in the two sampling zones via the ASIC, and resulting voltages, and voltage/current phase differences arising from liquid samples within those sensing zones, may be determined.

In particular, when an AC current signal is driven across a pair of drive electrode terminals of the first or second group of electrode terminals, a blood sample bridging the drive gap between those electrode terminals responds in such a way as to present an electrical impedance (Z, ohms). This manifests itself in that an AC electrical potential difference is generated across the sample, as measured by/between the two sensing electrode terminals in the given group of terminals, which is not in temporal phase with the AC current signal. The sample possesses not only a resistance (R, ohms) which is dissipative (real), but also a reactance (X, ohms) which is non-dissipative (imaginary).

Thus, if the driving AC current of amplitude |I| and angular frequency ω is represented by:

$$I=|I|\exp\{j(\omega t+\theta_1)\}$$

where $j=\sqrt{-1}$, and $\theta_1$ is the temporal phase of the sine wave AC current signal, then the resulting voltage across the two sensing electrodes of the given group of electrodes is represented by:

$$V=|V|\exp\{j(\omega t+\theta_V)\}$$

where $\theta_V$ is the temporal phase of the sine wave AC voltage signal of amplitude $|V|$ and angular frequency $\omega$.

The impedance of the sample is given by:

$$Z=|Z|\exp\{j\phi\}$$

where $|Z|$ is the magnitude of the impedance and $\phi$ is its phase angle.

The resistance of the blood sample (R) is given by:

$$R=|Z|\cos(\phi)$$

And the reactance of the blood sample (X) is given by $$X=|Z|\sin(\phi)$$

where $|Z|$ is measurable using the known amplitudes $|I|$ and $|V|$ of the applied current and resulting voltage signals respectively. Similarly, the phase angle of the impedance can be determined by applying Ohm's law:

$$V=|V|\exp\{j(\omega t+\theta_V)\}=I\times z=|I|\times|Z|\exp\{j(\omega t+\theta_1+\phi)\}$$

thus $$\phi=\theta_V-\theta_I=\omega\times\Delta t$$

where $\Delta t$ is the time lag between a peak in the applied AC sinewave current signal and a measured peak in the resulting AC voltage across the blood sample.

Thus, the resistance (R) and reactance (X) values of the blood sample may be determined from the AC current peak/amplitude value ($|I|$) as applied at a frequency $\omega$ between the two drive electrode terminals in a sampling zone, the resulting AC voltage peak/amplitude ($|V|$) as measured between the sensing electrodes in that sampling zone, and the time lag ($\Delta t$) between those two peaks in succession, as follows:

$$R = \left|\frac{V}{I}\right|\cos(\omega\times\Delta t) \quad \text{Equation (1)}$$

$$X = \left|\frac{V}{I}\right|\sin(\omega\times\Delta t) \quad \text{Equation (2)}$$

These values are either known by, or measured by, the sampling unit using the ASIC as described above, and the microcontroller (55) is arranged to calculate these resistance and reactance values.

A control register unit (91) is provided on the ASIC and is arranged to control, under overall control of the microprocessor via an interface unit (SPI), the timings and orchestration of control signals for operation of the amplifiers (/en signals to "enable" amplifiers), filters, switches and other components on the ASIC. The control register may be of a type such as would be readily apparent to the skilled person.

A thermo-couple (88) is formed in the ASIC and is electrically connected between a signal port of the control register unit (91) and an earth terminal and is arranged in the sampling device to make physical contact with a part of the sampling plate when the sampling plate is operatively connected to the sampling device in use. The control register unit is arranged to receive signals from the thermo-couple representative of the temperature of the sampling plate (30) and to convey those signals to the microcontroller to permit the temperature of the sampling plate to be determined by the microcontroller.

In use, the sampling unit is operable as follows. Once a user has applied a blood sample to the first and second sampling zones (FIG. 4; 2a, 2b) of the sampling plate (30), the blood sample is split between the first sampling zone (2a) dedicated to measuring haematocrit, and the second sampling zone (2b) dedicated to measuring HbA1c. The GOx/GDH spot (38) provided in the second sampling zone reacts with the free glucose present in the blood plasma of the blood sample within that zone to substantially oxidise it. A suitable period of time is allowed for this process (several seconds, e.g. between 0.5 and 15 seconds). This has been found to be as little as 0.5 seconds. It may be slowed by using a mediator which would allow the signal transient to be recorded over a time frame sufficient to determine the level of free glucose in the sample. For the determination of HbA1c, it is only required that the free glucose is oxidised, therefore it is important at least to see that a transient has occurred and decayed before the HbA1c measurement sequence is started. Subsequently, the blood-bearing sampling strip is electrically connected to the sampling unit (if not already so connected) as shown in FIG. 4 and FIG. 6.

The microcontroller shown in FIG. 6 is arranged to supply to the first pre-amplifier (63) of the ASIC (50) an alternating (AC) electrical current having a 1 MHz frequency, via the 1 MHz sinewave filter unit (67), to drive that current through the blood sample bridging the two drive electrodes within the second sampling zone, thereby to generate a first alternating potential difference across the spacing between the drive electrode terminals measurable via the two sensing electrode terminals (5b, 6b) within that sampling zone. This state is maintained for a period of time of several milliseconds in duration (e.g. between about 20 ms and about 200 ms or less). Subsequently, the microcontroller is arranged to apply a substantially constant direct (DC) voltage to the first pre-amplifier unit (63) of the ASIC to output to the first output port of the ASIC (65) a substantially constant DC offset of about 0.25 volts in combination with the 1 MHz AC current signal concurrently being applied to the second sampling zone. The microcontroller is arranged to then employ the peak detector unit and the phase-to-voltage unit of the ASIC to measure the amplitude of the voltage across the two sensing electrode terminals (5b, 6b) in the first sampling zone, and the time lag between the successive occurrences of a peak in the applied AC current and the resulting AC voltage, and to measure a first value of the electrical reactance ($X_1$) of the blood sample according to Equation (2) above.

The microcontroller is arranged to subsequently not apply the DC voltage offset and to continue to apply the 1 MHz AC current signal to the first and second drive electrode terminals of the second sampling zone. After a suitable time period following removal of the DC offset voltage (e.g. between about 20 ms and about 200 ms or less), the microcontroller is arranged to then employ the peak detector unit and the phase-to-voltage unit of the ASIC to measure the amplitude of the voltage across the two sensing electrode terminals (5b, 6b) in the first sampling zone, and the time lag between the successive occurrences of a peak in the applied AC current and the resulting AC voltage, and to measure a second value of the electrical reactance ($X_2$) of the blood sample according to Equation (2) above.

Either before, during or after performing the above process on the blood sample within the second sampling zone, the microcontroller is arranged to determine the haematocrit (HCT) within the blood sample as follows.

The microcontroller is arranged to supply a 50 KHz AC current to the analogue switch unit (69) of the ASIC via the 50 KHz sinewave filter unit (68) and to control the switch unit to connect the 50 KHz AC current to the second output port (72) of the ASIC via the second pre-amplifier unit (71). This causes the AC signal to be applied to the drive electrode terminals (3a, 4a) of the first sample zone, an alternating electrical current having a first signal frequency of 50 KHz to generate a first alternating potential difference of 50 KHz across the spacing between the electrode terminals, as measured by the two sensing electrodes (5b, 6b) in the first sample zone.

The microcontroller is arranged to then employ the peak detector unit and the phase-to-voltage unit of the ASIC to measure the amplitude of the voltage across the two sensing electrode terminals (5a, 6a) in the first sample zone, and the time lag between the successive occurrences of a peak in the applied AC current and the resulting AC voltage, and to measure a first value of the electrical resistance ($R_1$) of the blood sample according to Equation (1) above.

The microcontroller is arranged to then supply a 1 MHz AC current to the analogue switch unit (69) of the ASIC via the 1 MHz sinewave filter unit (67) and to control the switch unit to connect the 1 MHz AC current to the second output port (72) of the ASIC via the second pre-amplifier unit (71). This causes the 1 MHz AC signal to be applied to the drive electrode terminals (3a, 4a) of the first sample zone, an alternating electrical current having a second signal frequency of 1 MHz to generate a second alternating potential difference of 1 MHz across the spacing between the electrode terminals, as measured by the two sensing electrodes (5a, 6a) in the first sample zone.

The microcontroller is arranged to then employ the peak detector unit and the phase-to-voltage unit of the ASIC to measure the amplitude of the voltage across the two sensing electrode terminals (5a, 6a) in the first sample zone, and the time lag between the successive occurrences of a peak in the applied AC current and the resulting AC voltage, and to measure a second value of the electrical resistance ($R_2$) of the blood sample according to Equation (1) above, and to measure a third value of the electrical reactance ($X_3$) of the blood sample in the first sample zone according to Equation (2) above.

The microcontroller is arranged to subsequently calculate a value for the relative volume of red blood cells (haematocrit, HCT) in the liquid sample according to the first electrical resistance value, the second electrical resistance value and the third electrical reactance value according to the following formula, and store the result and/or to output the result to the user:

$$HCT = \left[ A\ln\left(\frac{R_1}{R_2}\right) + B\ln(X_3 + X_0) - C \right] \quad \text{Equation (3)}$$

Where A, B and C are constants associated with the sampling plate in question. For example, the values of A, B and C may each typically be within the range from about 0.05 to about 0.5, or preferably between about 0.1 and 0.25, or more preferably between about 0.1 and about 0.2. For example, when using electrodes formed from gold having a sheet resistance of 5 ohms per square, and the geometry illustrated in FIG. 4, the values in question may be:

A=0.142;
B=0.155;
C=0.157.

Actual values, suited to a given sampling zone geometry and electrode structure and material, may be determined by routine calibration employing commercially available blood samples of known HCT, as will be apparent to the skilled person. The value of $X_0$ may simply be zero, or may be adjusted if necessary to improve the predictive accuracy of the equation. It has been found that the term A is correlated with the conductivity of the electrode terminals of the sensing strip. The term B has been found to correlate with the resistivity of the interface (e.g. the wetting) between the blood sample and the electrode terminals in the sample zone. This is influenced by the electrode material (e.g. Gold), and the quality of the structure (e.g. roughness) of the electrode surfaces. The term C has been found to correlate with the variability of the average blood cell size (e.g. determined for "unfixed" or un-glycated blood cells) within the sample. This can be strongly influenced by ethnicity, blood type and interferences such as those which will be readily apparent to the skilled person. Values of C associated with different ethnicities (or blood type or known interferences) may be stored in a look-up table within (or accessible by) the control processor for suitable selection during calibration.

Table 1 shows examples of values of haematocrit for a blood sample of type A calculated according to the above method and equations. Three groups of ten measurements were made using the strip design illustrated in FIGS. 1, 3, 4 and 6 for measuring HCT. In each of the three groups a sample of blood was used having a known HCT value, namely 52%, 42% and 31%. Measurements of resistances $R_1$, and $R_2$ and reactance $X_3$ were made at 50 KHz and 1 MHz AC signal frequency respectively, and input into Equation (3) to generate a measurement value of HCT in each of the measurements. The ten measurements for each one of the three different common (known) HCT value shows a consistently accurate HCT measurement.

The microcontroller is arranged to then generate a value representing the concentration of glycated haemoglobin (HbA1c) in the blood within the sample according to the first electrical reactance value, the second electrical reactance value and a value of the relative volume of red blood cells in the liquid sample (haematocrit, HCT) according to the following formula, and store the result and/or to output the result to the user:

$$HbA1c = 100 \times \left(1 - \frac{X_1}{HCT \times X_2}\right) \quad \text{Equation (4)}$$

The quantity $X_1$ represents the reactance of a blood sample due to glycated red blood cells in the blood within the second sampling zone from which free glucose has been substantially oxidized by GOx/GDH, whereas $X_2$ represents the reactance of the whole blood sample in which both plasma and red blood cells contain glucose. The proportion of that reactance due to red blood cells is determined by the (HCT)×($X_2$) according to the haematocrit of the sample in the first sampling zone.

Figure 7:
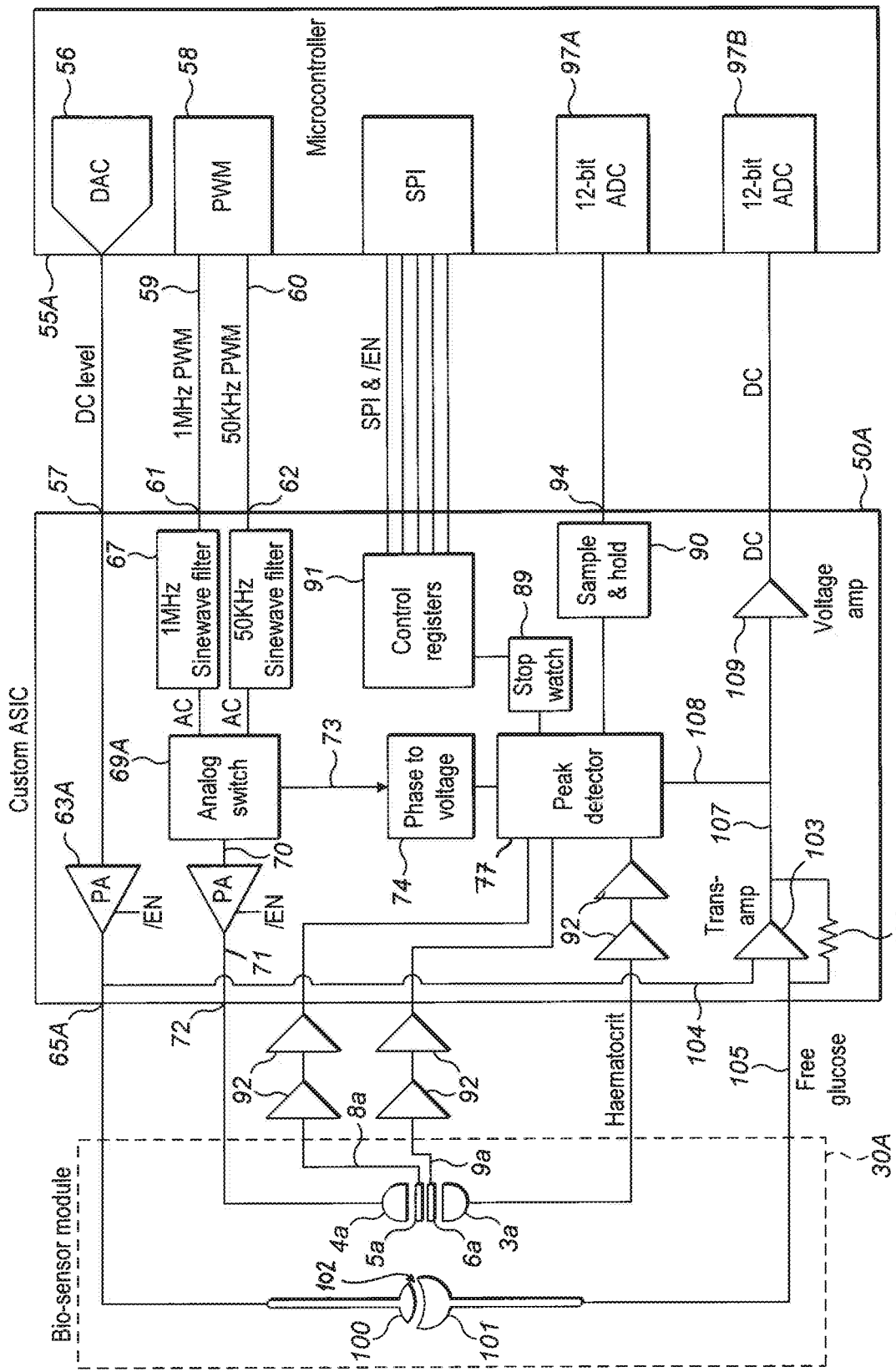
FIG. 7 schematically shows a sampling plate and sampling unit containing an ASIC comprising circuitry components adapted to implement signal generation and reception to and from a sampling plate.

FIG. 7 shows an alternative form of sampling strip and sampling unit to read the sampling strip for the purposes of measuring haematocrit alone.

This alternative sampling strip (30A) comprises a first sampling zone containing a first group of electrodes identical to the electrode group illustrated in FIGS. 1 to 3, and in the first sampling zone (2a) of the sampling strip of FIG. 4 and FIG. 6. The first group of electrodes comprises a pair of drive electrode terminals (3a, 4a) defining a drive gap within which are arranged two sensing electrode terminals (5a, 6a) for sensing a voltage drop across a blood sample when bridging the drive gap resulting from the an AC current driven between the two drive electrode terminals. The first group of electrodes, and the circuit elements of the ASIC (50A) with which they are arranged to electrically connect (shown as connected in FIG. 7) are the same as those elements of the ASIC (50) illustrated above in FIG. 6. Those circuit elements are arranged to operate, and be controlled by the microcontroller (55A) substantially as described above with reference to the first sample zone of the sample strip of FIG. 6 for determining a measure of haematocrit using equation (3) above.

However, the second sampling zone of this alternative sampling strip comprises a single pair of drive electrodes terminals (100, 101) defining between them a curved drive gap (102). The drive electrode pair is arranged to connect electrically to the ASIC to apply a DC electrical voltage (preferably substantially constant in value) across the curved drive gap when/if bridged by a blood sample within the second sensing zone. A deposit of a reagent, such as an enzyme or the like, to react with glucose in the blood sample (e.g. glucose oxidase (GOX) or glucose dehydrogenase (GDH)) is provided on the surface of the anode (e.g. electrode terminal 101) of the two drive electrodes. Like items are assigned like reference symbols as between FIGS. 6 and 7.

The ASIC (50A) in this alternative design differs from the ASIC of FIG. 6 in that the analogue switch unit (69A) does not provide a 1 MHz AC current input (66, FIG. 6) to the first pre-amplifier unit (63). The first pre-amplifier unit (63A) does not possess a feed-back loop (64, FIG. 6) and simply receives from the microcontroller a DC voltage signal (most preferably substantially constant), which it amplifies and outputs the result to a first voltage output port (65A) of the ASIC for electrical connection to a drive electrode (100) of the second sample zone.

The DC voltage signal is output by the microcontroller (55A) via a digital-to-analogue converter (56) and input to an amplifier (63A) formed within the ASIC the amplified output of which is input to a voltage output port (65A) of the ASIC and to a first input port (104) of an operational amplifier unit (103) formed in the ASIC. The operational amplifier has a second input port (105) which serves as voltage input terminal of the sensing unit respectively connected to an anode terminal (101) of the second pair of drive electrodes of the sample plate when the latter is connected to the former in use as shown in FIG. 7.

The operational amplifier has a respective output port (107) which is connected to its second input port via a feed-back loop comprising a resistor (106). As a result, the DC drive voltage (Vdrive) applied to the first input port of the operational amplifier by the first amplifier unit (63A) is expressed as a correspondingly substantially constant voltage level at the second input port (105) of the operational amplifier. This produces a controllably constant potential difference across the drive electrodes of the electrode pair (100, 101) in the second sample zone relative to a reference voltage (Vret). Consequential conduction through a blood sample in the second sample zone of the sampling strip enters the operational amplifier electrically connected to that blood sample. The result is that a measurable current is received by the operational amplifier at its second input port (105). This current is output on the output port (107) of the operational amplifier via a voltage amplifier (109) to a 12-bit analogue to digital converter (97B) of the microcontroller for use thereby in determining a value for the blood glucose level within the sample in the second sample zone, as described below. The measured current is also input from the operational amplifier to an input port of the peak detector unit (77) which is arranged to detect the occurrence of a peak in the detected current from the second sample zone, and to communicate the time of that occurrence to the microcontroller (55A) via a 12-bit analogue to digital converter (97B) of the microcontroller for use thereby in determining a value for the blood glucose level within the sample in the second sample zone, as described below.

It has been found that a direct (DC) voltage held between the two drive electrodes of the second sample zone, and thereby applied across the blood sample located there during the enzyme (GOX/GDH) reaction period, will cause a time-varying current to pass through the blood sample. Variation is believed to result, in part, from the changing (falling) quantity of free glucose within the plasma of the sample resulting in a changing electrical resistance of the plasma component of the blood. Most preferably, the DC voltage is substantially constant for simplicity, however non-constant DC voltages (e.g. smoothly falling or rising in a controlled way) could be employed if desired, though this is likely to complicate design and operation of the apparatus and so a substantially constant DC voltage is preferred.

Starting with an initial rise (near instantaneous) in current to a peak value at a time "$t_{peak}$", the observed quantity of current falls monotonically as glucose is increasingly oxidised in the blood plasma. Sample temperature affects the rate of decay of the current—lower temperatures result in faster decay. It has been found that the rate of fall of the observed current, following the peak current value, is characteristic of the amount of glucose originally present in the plasma of the blood sample before the oxidisation process began. The observed current decay is highly reproducible when the process is repeated. Thus, by performing this process initially with a sufficient plurality a blood samples each having an incrementally different, known quantity of glucose in its plasma component, one may build-up a plurality of reference curves of the type described above (or data sets representative of them) from which a future blood plasma glucose measurement may be made by reference. That is to say, with the plurality of reference curves (or representative data) one may perform a contemporaneous blood sampling operation as described above so as to generate a measurable current varying generally according to the current decay curve described above. By measuring a particular current value at a selected time during that current decay (i.e. a point along the contemporaneous current decay curve) one may subsequently identify a blood plasma glucose level associated with that current value as derived from a reference curve. The contemporaneously measured blood plasma glucose level may then be concluded to have the same glucose level. A Look-Up Table (LUT) or other storage may be used for this purpose. The process may include measuring a contemporaneous value "$I_m$" of the decaying current at a specified time "$t_m$" following the time "$t_{peak}$" at which the detected peak of the measured current occurs— the specified time having also been used when generating the reference curves. This current value then identifies the glucose value stored in the LUT associated with the reference curve which had the same current value at the same specified time in its current decay phase. The stored value from the LUT which matches a contemporaneous value will identify the associated blood plasma glucose level so measured. The specified time ($t_m$) may be between about 1 sec. and about 15 sec. Different reference curves or LUTs may be used according to the measured temperature of the sensing strip, as determined by the thermocouple described herein for example.

In this way, the microcontroller is arranged to apply a DC voltage to the pair of drive electrodes (100, 101) in the second sample zone, and to measure the resulting current.

The sampling unit contains such a LUT as described above, and is arranged to compare respective contemporaneously measured current (decaying) values separately from the second sample zone, with stored reference current values, to identify the closest match (or interpolate between the closest two matches) and to retrieve an associated blood plasma glucose value "$BG_{raw}$" from the LUT associated with that match. There may comprise as plurality of LUTs which may be respectively associated with reference curves generated for a common specified temperature of blood sample. The calculating unit may be arranged to select the appropriate LUT based on the measured temperature of the sampling strip at the time of the measurement at hand. A thermo-couple (not shown) may be provided in the sampling unit to physically contact the sampling plate (30A) in use and provide signals to which the microcontroller is responsive to determine a temperature of the sampling plate and, from that determination, select the most appropriate LUT for use as described above. Alternatively, through testing various temperatures, a temperature correction factor ($T_c$) may be determined and used to compensate the measurement for temperature effects. One LUT for Im and tm may then be used and the value retrieved from the LUT using $I_m$ and $t_m$ may then be adjusted using the temperature correction factor ($T_c$) as appropriate.

The microcontroller is arranged to produce an adjusted value "$BG_{corrected}$" for the blood plasma glucose level so retrieved according to:

$$BG_{corrected} = f(BG_{row}, HCT) \qquad \text{Equation (5)}$$

where $f(BG_{row}, HCT)$ is a predetermined corrective function of the measured haematocrit value HCT for the sample in the first sample zone, and of $BG_{row}$ which is an uncorrected blood plasma glucose value measured for the blood sample in the second sample zone. The form of the function $f(BG_{row}, HCT)$ of the predetermined corrective function may be selected by the user.

One example is of the form:

$$f(BG_{row}, HCT) = BG_{row} - [m \times (HCT) + c]$$

where m is a positive or negative constant and c is a positive or negative constant. These values may be evaluated by calibration against commercially available calibration blood samples containing known HCT and glucose levels. This functional form exploits the finding that errors in uncorrected glucose measurements are typically linear to a first approximation, as a function of HCT, and that so too is the corrective function. Of course, other more accurate corrective functional forms may be used such as would be apparent to the skilled person in this field.

The ASIC controller unit (91) controls the timing and coordination of the components formed upon the ASIC under the master control of the microcontroller via an interface (SPI) of the microcontroller with which the ASIC control unit is in communication. In this way, the required current and voltage values may be applied to, and received from, the first sample zone containing the first group of electrodes (3a, 4a, 5a, 6a) of the sampling plate (30A) via the ASIC to enable the microcontroller to perform the measurements of HCT and blood glucose as described above using equation (3).

This value of HCT is employed by the microcontroller to calculate an adjusted value of blood glucose in the sample of blood using the blood glucose value determined from the second sampling zone containing the second group of electrodes (100, 101).

Examples of the HCT value determined by the microcontroller using the ASIC and the first group of electrodes (3a, 4a, 5a, 6a) in the first sampling zone, as described above with relation to FIGS. 1, 3 and 6, and employed in Equation (3), are given in Table 1.

Aspects of the invention are defined by the following numbered paragraphs:

Paragraph 1: A sampling apparatus for use in performing electrical measurements on a liquid sample containing blood, the apparatus comprising: two (or more) current output terminals for outputting an alternating current signal applied therebetween; an alternating electrical current unit in electrical communication with the two (or more) current output terminals for applying thereto an alternating electrical current of a given amplitude and frequency when a said liquid sample is in electrical connection between the two (or more) current output terminals; a voltage unit in electrical communication with the two (or more) current output terminals for applying therebetween a direct (DC) electrical potential difference of a given magnitude; a first voltage input terminal for receiving a first electrical signal externally input thereto and a separate second voltage input terminal for receiving a second electrical signal externally input thereto when said liquid sample is in electrical connection between the first and second voltage input terminals; voltage detector(s) for measuring a first voltage and a second voltage using said first and second electrical signals, respectively; a control unit arranged to control the electrical current unit to apply a said alternating electrical current of said given frequency and concurrently to control the voltage unit and the voltage detector(s) to measure said first and second voltages both when said direct electrical potential difference is applied and when said direct electrical potential difference is not applied; a calculating unit arranged to calculate a first electrical reactance value using the first and second voltages measured when said direct electrical potential difference is applied, and to calculate a second electrical reactance value measured when said direct electrical potential difference is not applied; wherein the calculating unit is arranged to generate a value representing the concentration of glycated haemoglobin (HbA1c) in the liquid sample according to the first electrical reactance value, the second electrical reactance value and a value representing the relative volume of red blood cells in the liquid sample (haematocrit).

Paragraph 2: A sampling apparatus according to Paragraph 1 in which the given frequency has a value in the range 500 KHz to 1.5 MHz.

Paragraph 3: A sampling apparatus for use in performing electrical measurements on a liquid sample containing blood, the apparatus comprising: two (or more) current output terminals for outputting an alternating current signal applied therebetween; an alternating electrical current unit in electrical communication with the two (or more) current output terminals for applying therebetween an alternating electrical current of a given amplitude and frequency, when a said liquid sample is in electrical connection between the two (or more) current output terminals; a first voltage input terminal for receiving a first electrical signal externally input thereto and a separate second voltage input terminal for receiving a second electrical signal externally input thereto, when said liquid sample is in electrical connection between the first and second voltage input terminals; voltage detector(s) for measuring a first voltage and a second voltage using said first and second electrical signals, respectively; a control unit arranged to control the electrical current unit to apply a said alternating electrical current at a first frequency and concurrently to control the voltage detector(s) to measure said first and second voltages, and to further control the electrical current unit to apply said alternating electrical current at a second frequency exceeding the first frequency and concurrently to control the voltage detector(s) to measure said first and second voltages; a calculating unit arranged to calculate a first electrical resistance value using the first and second voltages measured at said first frequency, and a second electrical resistance value and a reactance value using said first and second voltages measured at said second frequency; wherein the calculating unit is arranged to generate a value representing the relative volume of red blood cells in the liquid sample (haematocrit) according to the first and second electrical resistance values and the electrical reactance value.

Paragraph 4: A sampling apparatus according to Paragraph 1 and Paragraph 3 arranged to generate both said value representing the relative volume of red blood cells in the liquid sample (haematocrit) and to generate said value representing the concentration of glycated haemoglobin (HbA1c) in a liquid sample using said haematocrit value.

Paragraph 5: A sampling apparatus according to any of Paragraphs 1 to 4 including the sampling plate according to any of claims 1 to 14 in which each one of said two drive electrodes of the sampling plate is adapted to electrically connect to a respective one of said two (or more) current output terminals concurrently, and in which each one of said two sensing electrodes is adapted to electrically connect to a respective one of the first voltage input terminal and the second voltage input terminal concurrently, thereby to connect the two drive electrodes and the two sensing electrodes to the sampling apparatus simultaneously for electrical communication therewith.

Paragraph 6: A sampling apparatus according to any of Paragraphs 1 to 5 comprising an integrated circuit arranged for measuring said first voltage and said second voltage, and responsive to the control unit to apply said alternating current accordingly.

Paragraph 7: A sampling apparatus according to any of Paragraphs 1 to 6 in which the first frequency has a value in the range 1 KHz to 150 KHz.

Paragraph 8: A sampling apparatus according to any of Paragraph 1 to 7 in which the second frequency has a value in the range 500 KHz to 1.5 MHz.

Paragraph 9: A sampling apparatus according to any of Paragraph 1 to 8 in which said direct (DC) voltage is substantially constant in value.

Paragraph 10: A sample measurement method for performing electrical measurements on a liquid sample containing blood, the method comprising: receiving the liquid sample on a sample plate comprising electrode terminals which are separated by a spacing adapted to be bridged by blood from the liquid sample and which comprise a reagent to react with free glucose in the liquid sample; and applying to the electrodes an alternating electrical current having a given frequency to generate a first alternating potential difference across the spacing between the electrode terminals; applying between the electrode terminals a substantially direct (DC) electrical potential difference of a given magnitude; determining a value of a first electrical reactance of the liquid sample bridging said spacing for said given frequency; removing the substantially direct (DC) electrical potential difference from between the two electrode terminals; applying to the electrodes the alternating electrical current having said given frequency to generate a second alternating potential difference across the spacing between the electrode terminals; determining a value of a second electrical reactance of the liquid sample bridging said spacing for said given frequency; generating a value representing the concentration of glycated haemoglobin (HbA1c) in the blood within the sample according to the first electrical reactance value, the second electrical reactance value and a value of the relative volume of red blood cells in the liquid sample (haematocrit).

Paragraph 11: A sample measurement method for performing electrical measurements on a liquid sample containing blood, the method comprising: receiving the liquid sample on a sample plate comprising electrode terminals which are separated by a spacing adapted to be bridged by blood from the liquid sample; and applying to the electrodes an alternating electrical current having a first signal frequency to generate a first alternating potential difference across the spacing between the electrode terminals; determining a value of a first electrical resistance of the liquid sample bridging said spacing for said first signal frequency; applying to the electrodes an alternating electrical current having a second signal frequency exceeding said first signal frequency to generate a second alternating potential difference across the spacing between the electrode terminals; determining a value of a second electrical resistance and a value of a reactance of the liquid sample bridging said spacing for said second signal frequency; generating a value for the relative volume of red blood cells (haematocrit) in the liquid sample according to the first electrical impedance value and the second electrical impedance value.

Paragraph 12: A sample measurement method according to Paragraph 10 including generating said value representing the relative volume of red blood cells in the liquid sample (haematocrit) according to Paragraph 11.

Paragraph 13: A sample measurement method according to any of Paragraphs 10 to 12 in which said direct (DC) voltage is substantially constant in value.

The embodiments of the invention described above are intended to be illustrative of preferred implementations of the invention and variants, modifications and alterations to those implementations, such as would be readily apparent to the skilled person, are encompassed within the scope of the invention as defined e.g. by the claims.

TABLE 1

| STRIP NO. | $R_1$ | $R_2$ | $X_3$ | MEASURED HCT | ACTUAL HCT |
|---|---|---|---|---|---|
| 1 | 318.2 | 232.3 | 58 | 51.7049034 | 52 |
| 2 | 320.1 | 234.7 | 59 | 51.9084503 | |
| 3 | 318.7 | 232.9 | 58 | 51.6905695 | |
| 4 | 320.2 | 233 | 58 | 51.751151 | |
| 5 | 318.2 | 232.1 | 58 | 51.7171343 | |
| 6 | 318.3 | 232.2 | 58 | 51.7154794 | |
| 7 | 318.4 | 232.2 | 58 | 51.7199399 | |
| 8 | 317.5 | 230.5 | 57 | 51.5145174 | |
| 9 | 319.2 | 232.6 | 58 | 51.7311329 | |
| 10 | 320.05 | 232.8 | 58 | 51.7566914 | |

| Strip No. | $R_1$ | $R_2$ | $X_3$ | Measured HCT | Actual HCT |
|---|---|---|---|---|---|
| 1 | 240 | 190.3 | 35 | 42.7028225 | 42 |
| 2 | 240.3 | 190.5 | 35 | 42.7056454 | |

TABLE 1-continued

| | | | | | |
|---|---|---|---|---|---|
| 3 | 240.7 | 190.4 | 35 | 42.7367189 | |
| 4 | 241 | 190.8 | 35.5 | 42.9444675 | |
| 5 | 240.7 | 190.5 | 35 | 42.7292629 | |
| 6 | 240.9 | 190.9 | 35.5 | 42.9311337 | |
| 7 | 240.7 | 190.8 | 35 | 42.7069183 | |
| 8 | 241 | 191 | 36 | 43.1463773 | |
| 9 | 241.3 | 191.2 | 35 | 42.7125328 | |
| 10 | 240 | 190.2 | 35 | 42.7102863 | |
| 1 | 195.3 | 165.8 | 18 | 31.4260775 | 31 |
| 2 | 193.1 | 163.8 | 18 | 31.4375429 | |
| 3 | 194.7 | 165.2 | 18 | 31.4338656 | |
| 4 | 194.3 | 165.3 | 18 | 31.3960694 | |
| 5 | 193.1 | 163.7 | 18 | 31.4462147 | |
| 6 | 193.1 | 163.8 | 18 | 31.4375429 | |
| 7 | 193.1 | 163.7 | 18 | 31.4462147 | |
| 8 | 192.5 | 163.6 | 18 | 31.4107008 | |
| 9 | 192.7 | 163.6 | 18 | 31.4254464 | |
| 10 | 192.8 | 163.5 | 18 | 31.4414958 | |

The invention claimed is:

1. A sampling plate comprising:
a sample zone for receiving a liquid sample;
two drive electrodes with separate respective electrode terminals spaced within the sample zone by a spacing for receiving said liquid sample within the sample zone for use in driving an electrical signal through the sample;
two sensing electrodes with separate respective electrode terminals spaced within the sample zone between the electrode terminals of the two drive electrodes within the sample zone for use in sensing an electrical signal generated by the drive electrodes within said sample.

2. A sampling plate according to claim 1 in which the two sensing electrode terminals present to each other opposing sides which define between them an elongate sensing gap extending along the sample zone for receiving said sample therein.

3. A sampling plate according to claim 2 in which the width of the sensing gap is greater than about 90 microns and less than about 160 microns.

4. A sampling plate according to claim 2 in which the sensing gap has a substantially uniform width along at least a part of its length.

5. A sampling plate according to claim 2 in which the two drive electrode terminals present to each other opposing sides which define between them an elongate drive gap extending along the sample zone for receiving said sample therein whereby the drive electrodes are adapted to drive electrical signal transversely across the drive gap wherein the drive gap has a substantially uniform width along at least a part of its length.

6. A sampling plate according to claim 2 in which the two sensing electrode terminals present to each other opposing sides which define between them an elongate sensing gap extending along the sample zone for receiving said sample therein, and in which the sensing gap and/or the drive gap has a substantially uniform width along at least a part of its length.

7. A sampling plate according to claim 1 in which the two drive electrode terminals present to each other opposing sides which define between them an elongate drive gap extending along the sample zone for receiving said sample therein whereby the drive electrodes are adapted to drive electrical signal transversely across the drive gap.

8. A sampling plate according to claim 7 in which the sensing gap extends along the drive gap.

9. A sampling plate according to claim 8 in which the two sensing electrode terminals present to each other opposing sides which define between them an elongate sensing gap extending along the sample zone for receiving said sample therein, and in which the sensing gap and/or the drive gap has a substantially uniform width along at least a part of its length.

10. A sampling plate according to claim 1 in which a said drive electrode terminal and an adjacent sensing electrode terminal present to each other opposing sides which define between them an elongate partitioning gap extending along the sample zone to define a partition between the adjacent terminals within the sample zone.

11. A sampling plate according to claim 10 in which the partitioning gap has a substantially uniform width along at least a part of its length.

12. A sampling plate according to claim 10 in which the width of the partitioning gap is about 1.5 times the width of the sensing gap.

13. A sampling plate according to claim 1 in which the sensing electrode terminals are formed on a surface of the sampling plate within the sample zone.

14. A sampling plate according to claim 13 in which the drive electrode terminals are formed on a surface of the sampling plate in common with the sensing electrode terminals within the sampling zone.

15. A sampling plate according to claim 1 in which each of the drive electrodes and each of the sensing electrodes is in electrical communication with respective electrical contact zones provided on the sampling plate which are exposed for electrical connection simultaneously with an external drive current source and external sensing circuitry, respectively.

16. A sampling plate according to claim 1 in which the sample zone comprises a reagent to react with free glucose in the liquid sample.

17. A sampling plate according to claim 1 comprising a plurality of said sample zones for receiving said liquid sample, each with two drive electrodes with separate respective electrode terminals spaced by a spacing for receiving said liquid sample within each respective sample zone for use in driving an electrical signal through the sample, and each with two sensing electrodes with separate respective electrode terminals spaced between the electrode terminals of the two drive electrodes for use in sensing an electrical signal generated by the drive electrodes within said sample.

* * * * *